United States Patent
Pilcher

(10) Patent No.: US 6,720,180 B2
(45) Date of Patent: Apr. 13, 2004

(54) WOUNDED EPITHELIUM-SPECIFIC TRANSCRIPT

(75) Inventor: Brian K. Pilcher, Edmond, OK (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/859,961

(22) Filed: May 17, 2001

(65) Prior Publication Data

US 2003/0167478 A1 Sep. 4, 2003

Related U.S. Application Data

(60) Provisional application No. 60/269,873, filed on Feb. 15, 2001.

(51) Int. Cl.$^7$ ............................................. C12N 15/86
(52) U.S. Cl. .................. 435/320.1; 435/91.4; 536/23.5; 424/450
(58) Field of Search ............................ 435/320.1, 91.4; 536/23.5

(56) References Cited

PUBLICATIONS

Sambrook J. et al., in Molecular Cloning: a Laboratory Manual; Second Edition, 1989; pp. 17.2–17.5.*
JP Condreay et al., Proc.Natl.Acad.Sci. USA, "Transient and stable gene expression in mammalian cells transduced with a recombinant baculovirus vector," Jan. 1999, vol. 96, pp. 127–132.*
B Birren et al., Locus Accession No. AC004590, 1998.*
Chen et al., "Epsin is an EH–domain–binding protein implicated in clathrin–mediated endocytosis," Nature 394(6695), 793–797, 1998.
Clark et al., "Fibronectin and fibrin provide a provisional matrix for epidermal cell migration during wound reepithelialization," J. Invest. Dermatol., 79:264–269, 1982.
Clark, "Wound Repair. Overview and General Considerations," In: The molecular and cellular biology of wound repair., 2nd Ed. (Clark, Ed.), Plenum Press, New York, 3–50, 1995.
Coulombe, "Toward a molecular definition of keratinocyte activation after acute injury to stratified epithelia," Biochem. Biophys. Res. Commun., 236(2):231–238, 1997.
Drake et al., "Epsin binds to clathrin by associating directly with the clathrin–terminal domain," J Biol Chem 275(9), 6479–6489, 2000.
Grinnell, "The activated keratinocyte: up regulation of cell adhesion and migration during wound healing," J. Trauma 30:S144–S149, 1990.
Inoue et al., "Collagenase expresion is rapidly induced in wound–edge keratinocytes after acute injury in human skin, persists during healing, and stops at re–epithelialization," J. Invest. Dermatol. 104, 479–483, 1995.
McPherson et al., "EH domain–dependent interactions between Eps15 and clathrin–coated vesicle protein p95," Biochem Biophys Res Commun 244(3), 701–705, 1998.
Pilcher et al., "The activity of collagenase–1 is required for keratinocyte migration on a type 1 collagen matrix," J. Cell Biol 137(6), 1445–1457, 1997.
Rosenthal et al., "The epsins define a family of proteins that interact with components of the clathrin coat and contain a new protein module," J Biol Chem 274(48), 33959–33965, 1999.
Saarialho–Kere et al., "Distinct localization of collagenase and tissue inhibitor of metalloproteinases expression in wound healing associated with ulcerative pyogenic granuloma," J. Clin. Invest. 90:1952–1957, 1992.
Saarialho–Kere et al., "Cell–matrix interactions modulate interstitial collagenase expression by human keratinocytes actively involved in wound healing," J. Clin. Invest. 92:2858–2866, 1993.
Salcini et al., "Binding specifcity and in vivo targets of the EH domain, a novel protein–protein interaction module," Genes Dev 11(17), 2239–2249, 1997.
Spradling et al., "Cloning and initial characterization of human epsin 3, a novel matrix–induced keratinocyte specific transcript," J. Invest. Dermatology, 115(2):332, Abstract:HB5, 2000.
Sudbeck et al., "Induction and repression of collagenase–1 by keratinocytes is controlled by distinct components of different extracellular matrix compartments," J Biol Chem 272(35), 22103–22110, 1997.
Wang et al., "The appendage domain of α–adaptin is a high affinity binding site for dynamin," J Biol Chem 270(17), 10079–10083, 1995.

* cited by examiner

Primary Examiner—Dave T. Nguyen
Assistant Examiner—J. Eric Angell
(74) Attorney, Agent, or Firm—Fulbright & Jaworski L.L.P.

(57) ABSTRACT

The instant invention discloses compositions and methods related to epsin 3, a novel protein closely related to, but distinct from previously described epsins. Epsin 3 mRNA and protein are undetectable in keratinocytes isolated from unwounded skin, but is induced in cells following contact with fibrillar type I collagen. It is envisioned that this protein plays an important role in activated epithelial cells during tissue morphogenesis.

9 Claims, No Drawings

SEQUENCE LISTING

<160> NUMBER OF SEQ ID NOS: 6

<210> SEQ ID NO 1
<211> LENGTH: 2098
<212> TYPE: DNA
<213> ORGANISM: Homo Sapiens

<400> SEQUENCE: 1

| | | | | | |
|---|---|---|---|---|---|
| atgacgacct | ccgcactccg | gcgccaggtg | aagaacatcg | tgcacaacta ctccgaggca | 60 |
| gaaatcaagg | tgcgcgaggc | caccagcaat | gaccccctgg | gccccctag ttcgctcatg | 120 |
| tccgagatcg | ctgacctgac | cttcaacaca | gtggccttca | ccgaagtcat gggcatgctg | 180 |
| tggcggcggc | tcaatgacag | cggcaagaac | tggcggcacg | tgtacaaggc tctaacattg | 240 |
| ctggactacc | tgctcaagac | gggctccgag | cgggtggccc | accagtgccg cgagaacctc | 300 |
| tacaccatcc | agacactcaa | ggacttccag | tacatcgacc | gcgacggcaa ggaccagggc | 360 |
| gtcaacgtgc | gcgagaaggt | caagcaggta | atgccctgc | tcaaggatga ggagcggctg | 420 |
| cggcaggagc | gaacccacgc | cctcaagacc | aaggagcgca | tggcactgga gggcatcggc | 480 |
| attggcagtg | ggcagctggg | cttcagccgc | cgctacggcg | aggactacag ccgctcccgg | 540 |
| ggctccccgt | cctcctacaa | ctcctcctct | tcgtcacccc | gctatacctc cgacctggag | 600 |
| caggcccggc | ctcagacgtc | aggggaagag | gaactgcagc | tgcagctggc cctcgccatg | 660 |
| agccgtgagg | aggcagagaa | gcctgtcccc | ccagcctccc | acaggacga ggacctgcag | 720 |
| ctgcagctgg | ctctgcgcct | gagccggcag | gagcacgaga | aggaggtgag gtcctggcag | 780 |
| ggtgatggct | ccccccatggc | caatggtgca | ggggccgtgg | tccaccatca gcgggacaga | 840 |
| gagcctgaga | gagaagagag | aaaggaggag | gagaagctaa | aaaccagcca gtcctccatc | 900 |
| ctggacttgg | ctgacatctt | cgtacctgcc | ctggccccgc | cctccacaca ctgctctgct | 960 |
| gacccatggg | acatcccagg | ttttaggccg | aacacagagg | ccagtggatc ctcctgggg | 1020 |
| ccttctgcag | accctggtc | tccgatcccc | tcaggaaccg | tcctgtcccg aagccagccc | 1080 |
| tgggatctga | ctcccatgct | ctcctcctct | gagccctggg | gcaggacccc agtgctgcct | 1140 |
| gctgggcccc | ccaccacaga | ccctgggcc | ctgaactctc | ccaccacaa actcccagc | 1200 |
| actggggctg | accttgggg | agcctccctg | gagacctccg | acacacctgg tggtgcctcg | 1260 |
| acctttgacc | catttgccaa | acctccagaa | tccacagaga | ccaaggaggg gctggagcag | 1320 |
| gccctgccct | ctgggaagcc | cagcagccct | gtggagctgg | acctgtttgg agaccccagc | 1380 |
| cccagttcca | agcaaaatgg | cacgaaggag | ccagatgccc | tggacctggg catactaggg | 1440 |
| gaagcactaa | cccagccaag | caaagaggcc | cgagcttgcc | ggactcccga gtccttcctg | 1500 |
| ggtccctcag | cttcctcctt | ggtcaacctt | gactcgttgg | tcaaggcacc ccaggttgca | 1560 |
| aagacccgga | acccttcct | gacaggtctc | agcgctccgt | ccccccaccaa cccgttcggc | 1620 |
| gcgggcgagc | cggcaggcc | gacgctaaac | cagatgcgca | ccggctcgcc ggcgctgggc | 1680 |
| ctggcaggcg | ggcctgtggg | ggcgcccctg | ggctccatga | cctacagcgc ctctctgccc | 1740 |
| ctcccgctca | gcagcgtgcc | agctggcttg | accctccccg | cctcggttag cgtcttcccg | 1800 |
| caggccggag | ccttcgcacc | gcagccgctg | ctgcccacgc | cgagctcagc cgggccgcgg | 1860 |
| cccccgcccc | cgcagaccgg | caccaacccc | ttcctctgag | cccgcccg tcccatacg | 1920 |
| gcctgcgcct | gcgccggacg | ctccgcgccc | cgcctccgg | accggggct gggcggggc | 1980 |
| ccggtgctag | tggaacgccg | agccagtggc | ggctggtatc | ccgcggcggc tctggaagct | 2040 |

```
ggacgcggac cacggcccgg gagctagaaa ctgaacgccc gcataataaa gactggaa        2098
```

<210> SEQ ID NO 2
<211> LENGTH: 632
<212> TYPE: PRT
<213> ORGANISM: Homo Sapiens

<400> SEQUENCE: 2

```
Met Thr Thr Ser Ala Leu Arg Arg Gln Val Lys Asn Ile Val His Asn
1               5                   10                  15

Tyr Ser Glu Ala Glu Ile Lys Val Arg Glu Ala Thr Ser Asn Asp Pro
            20                  25                  30

Trp Gly Pro Pro Ser Ser Leu Met Ser Glu Ile Ala Asp Leu Thr Phe
        35                  40                  45

Asn Thr Val Ala Phe Thr Glu Val Met Gly Met Leu Trp Arg Arg Leu
    50                  55                  60

Asn Asp Ser Gly Lys Asn Trp Arg His Val Tyr Lys Ala Leu Thr Leu
65                  70                  75                  80

Leu Asp Tyr Leu Leu Lys Thr Gly Ser Glu Arg Val Ala His Gln Cys
                85                  90                  95

Arg Glu Asn Leu Tyr Thr Ile Gln Thr Leu Lys Asp Phe Gln Tyr Ile
            100                 105                 110

Asp Arg Asp Gly Lys Asp Gln Gly Val Asn Val Arg Glu Lys Val Lys
        115                 120                 125

Gln Val Met Ala Leu Leu Lys Asp Glu Glu Arg Leu Arg Gln Glu Arg
    130                 135                 140

Thr His Ala Leu Lys Thr Lys Glu Arg Met Ala Leu Glu Gly Ile Gly
145                 150                 155                 160

Ile Gly Ser Gly Gln Leu Gly Phe Ser Arg Arg Tyr Gly Glu Asp Tyr
                165                 170                 175

Ser Arg Ser Arg Gly Ser Pro Ser Ser Tyr Asn Ser Ser Ser Ser Ser
            180                 185                 190

Pro Arg Tyr Thr Ser Asp Leu Glu Gln Ala Arg Pro Gln Thr Ser Gly
        195                 200                 205

Glu Glu Glu Leu Gln Leu Gln Leu Ala Leu Ala Met Ser Arg Glu Glu
    210                 215                 220

Ala Glu Lys Pro Val Pro Pro Ala Ser His Arg Asp Glu Asp Leu Gln
225                 230                 235                 240

Leu Gln Leu Ala Leu Arg Leu Ser Arg Gln Glu His Glu Lys Glu Val
                245                 250                 255

Arg Ser Trp Gln Gly Asp Gly Ser Pro Met Ala Asn Gly Ala Gly Ala
            260                 265                 270

Val Val His His Gln Arg Asp Arg Glu Pro Glu Arg Glu Glu Arg Lys
        275                 280                 285

Glu Glu Glu Lys Leu Lys Thr Ser Gln Ser Ser Ile Leu Asp Leu Ala
    290                 295                 300

Asp Ile Phe Val Pro Ala Leu Ala Pro Pro Ser Thr His Cys Ser Ala
305                 310                 315                 320

Asp Pro Trp Asp Ile Pro Gly Phe Arg Pro Asn Thr Glu Ala Ser Gly
                325                 330                 335

Ser Ser Trp Gly Pro Ser Ala Asp Pro Trp Ser Pro Ile Pro Ser Gly
            340                 345                 350

Thr Val Leu Ser Arg Ser Gln Pro Trp Asp Leu Thr Pro Met Leu Ser
        355                 360                 365
```

```
Ser Ser Glu Pro Trp Gly Arg Thr Pro Val Leu Pro Ala Gly Pro Pro
    370                 375                 380

Thr Thr Asp Pro Trp Ala Leu Asn Ser Pro His His Lys Leu Pro Ser
385                 390                 395                 400

Thr Gly Ala Asp Pro Trp Gly Ala Ser Leu Glu Thr Ser Asp Thr Pro
                405                 410                 415

Gly Gly Ala Ser Thr Phe Asp Pro Phe Ala Lys Pro Pro Glu Ser Thr
                420                 425                 430

Glu Thr Lys Glu Gly Leu Glu Gln Ala Leu Pro Ser Gly Lys Pro Ser
            435                 440                 445

Ser Pro Val Glu Leu Asp Leu Phe Gly Asp Pro Ser Pro Ser Ser Lys
    450                 455                 460

Gln Asn Gly Thr Lys Glu Pro Asp Ala Leu Asp Leu Gly Ile Leu Gly
465                 470                 475                 480

Glu Ala Leu Thr Gln Pro Ser Lys Glu Ala Arg Ala Cys Arg Thr Pro
                485                 490                 495

Glu Ser Phe Leu Gly Pro Ser Ala Ser Ser Leu Val Asn Leu Asp Ser
                500                 505                 510

Leu Val Lys Ala Pro Gln Val Ala Lys Thr Arg Asn Pro Phe Leu Thr
    515                 520                 525

Gly Leu Ser Ala Pro Ser Pro Thr Asn Pro Phe Gly Ala Gly Glu Pro
    530                 535                 540

Gly Arg Pro Thr Leu Asn Gln Met Arg Thr Gly Ser Pro Ala Leu Gly
545                 550                 555                 560

Leu Ala Gly Gly Pro Val Gly Ala Pro Leu Gly Ser Met Thr Tyr Ser
                565                 570                 575

Ala Ser Leu Pro Leu Pro Leu Ser Ser Val Pro Ala Gly Leu Thr Leu
                580                 585                 590

Pro Ala Ser Val Ser Val Phe Pro Gln Ala Gly Ala Phe Ala Pro Gln
                595                 600                 605

Pro Leu Leu Pro Thr Pro Ser Ser Ala Gly Pro Arg Pro Pro Pro Pro
    610                 615                 620

Gln Thr Gly Thr Asn Pro Phe Leu
625                 630

<210> SEQ ID NO 3
<211> LENGTH: 13
<212> TYPE: DNA
<213> ORGANISM: Artificial Sequence
<220> FEATURE:
<221> NAME/KEY: misc_feature
<222> LOCATION: (1)..(13)
<223> OTHER INFORMATION: Artificial Primer

<400> SEQUENCE: 3
aagcttacga tgc                                                    13

<210> SEQ ID NO 4
<211> LENGTH: 17
<212> TYPE: DNA
<213> ORGANISM: Artificial Sequence
<220> FEATURE:
<221> NAME/KEY: misc_feature
<222> LOCATION: (1)..(17)
<223> OTHER INFORMATION: Artificial Primer

<400> SEQUENCE: 4
gctccaggtc ggaggta                                                17
```

```
<210> SEQ ID NO 5
<211> LENGTH: 17
<212> TYPE: DNA
<213> ORGANISM: Artificial Sequence
<220> FEATURE:
<221> NAME/KEY: misc_feature
<222> LOCATION: (1)..(17)
<223> OTHER INFORMATION: Artificial Primer

<400> SEQUENCE: 5
atgacgacct ccgcact                                                17

<210> SEQ ID NO 6
<211> LENGTH: 20
<212> TYPE: PRT
<213> ORGANISM: Human

<400> SEQUENCE: 6

Lys Gln Asn Gly Thr Lys Glu Pro Asp Ala Leu Asp Leu Gly Ile Leu
1               5                   10                  15

Gly Glu Ala Leu
            20
```

US 6,720,180 B2

WOUNDED EPITHELIUM-SPECIFIC TRANSCRIPT

This application claims priority to U.S. Provisional Application No. 60/269,873, which was filed on Feb. 15, 2001.

The government owns rights in the present invention pursuant to grants from the National Institutes of Health (NIH-NIAMS) and the NIH-funded UT Southwestern Skin Disease Research Center.

BACKGROUND OF THE INVENTION

1. Field of the Invention

The present invention relates generally to the fields of wound healing. More particularly, it concerns the cloning and characterization of the epsin 3 gene, a wounded epithelium-specific transcript.

2. Description of Related Art

The epidermis consists of a multilayered epithelial sheet that provides a physical barrier against the outside environment and heals in response to injury. In unwounded skin, basal keratinocytes reside on a basement membrane (BM) that physically separates these cells from the underlying dermal connective tissue rich in type I collagen. While in contact with this extracellular matrix (ECM), keratinocytes express a programmed subset of genes that promotes proliferation and differentiation. Following injury, however, keratinocytes from the surrounding tissue are activated by exposure to ligands released into the wound site and by contact with extracellular matrix macromolecules (Grinnell, 1990; Clark, 1996; Coulombe, 1997).

Normal cutaneous wound healing requires an orderly progression of events to re-establish the integrity of the injured tissue. The initial injury sets forth a programmed series of responses that include re-epithelialization, inflammation, angiogenesis, fibroplasia, matrix accumulation, and resolution (Clark 1992). In wounds that disrupt the BM, keratinocytes from the surrounding uninjured tissue are "activated" by exposure to soluble ligands released into the wound site and by contact with dermal and provisional extracellular matrix. This activation, which typically occurs 18–24 hours prior to the onset of migration and hyperproliferation, occurs as wound edge keratinocytes switch from a gene expression program of proliferation and differentiation to one that supports sustained and directed migration leading to re-epithelialization (Coulombe, 1997).

Migration of keratinocytes from the wound edge occurs as the cells dissect under a provisional matrix of fibrin and fibronectin (Clark et al., 1982) and over or through a viable dermis, which includes structural molecules distinct from those in the basement membrane. Loss of contact with the basement membrane and subsequent exposure to the underlying dermal matrix may be a critical determinant that alters gene expression and induces the activated keratinocyte phenotype. Recent evidence supports the idea that the enzyme, matrix metalloproteinase collagenase-1, is invariantly expressed in keratinocytes not in contact with a basement membrane, but rather in keratinocytes migrating over the dermal matrix and in close apposition to collagen fibers (Inoue et al., 1995; Saarialho-Kere et al., 1992; Saarialho-Kere et al., 1993; Pilcher et al., 1997). Moreover, expression of this enzyme is selectively induced in keratinocytes following contact with fibrillar type I collagen in vitro and its proteolytic activity is essential for cell migration across this matrix (Pilcher et al., 1997; Sudbeck et al, 1997). Together, these data suggest that keratinocyte contact with dermal extracellular matrix, and in particular fibrillar type I collagen, profoundly influence keratinocyte activation following injury by inducing the expression of transcripts required for efficient repair.

Many of the genes upregulated in keratinocytes during healing, including secreted proteinases and integrin receptors, enable a fundamental shift in cell behavior that supports sustained and directed migration to re-establish the normal cytoarchitecture of the skin (Coulombe, 1997). The preponderance of studies to date attempting to identify signals that stimulate keratinocyte activation during wound healing have focused on soluble mediators, whereas the role that alterations in cell:extracellular matrix interactions play in this process has received relatively little attention.

The epsins are a family of recently characterized genes involved in clathrin-mediated endocytosis. Epsins 1 and 2 function as molecular bridges to bind epidermal growth factor pathway substrate 15 (Eps15) and clathrin adaptor protein-2 (AP-2), allowing the appropriate molecular conformation required for assembly of the coated pit. Indeed, perturbation of epsin function in fibroblasts potently inhibits assembly and internalization of clathrin-coated pits (Chen et al., 1998; Rosenthal et al., 1999). Conserved domains common to all epsins include a COOH-terminal consensus sequence of three NPF repeats that bind Eps15, multiple central region DPW motifs that bind AP-2, and a 150 amino acid $NH_2$-terminal protein module, the epsin $NH_2$-terminal homology domain (ENTH domain).

SUMMARY OF THE INVENTION

The instant invention encompasses methods and compositions comprising the mammalian epsin 3 protein and the gene encoding said protein. An envisioned embodiment of the invention therefore comprises an isolated and purified polynucleotide comprising a nucleic acid sequence encoding a mammalian epsin 3 gene. This polynucleotide may be further defined as a nucleic acid encoding 10, 20, 40, 50, 60, 100 contiguous amino acid residues or the full-length protein of SEQ ID NO:2.

A further embodiment of the invention encompasses a polynucleotide comprising a nucleic acid sequence encoding SEQ ID NO:1 or at least 10, 20, 30, 50, 80 or 100 contiguous bases of SEQ ID NO:1. An additional embodiment of the invention as setforth herein is considered to comprise an epsin 3 protein, peptide or polypeptide. In an envisioned embodiment, such a protein, peptide or polypeptide may be further characterized as comprising at least 10, 20, 30, 50, 80 or 100 contiguous amino acids as set forth in SEQ ID NO:2 or the full length sequence set forth in SEQ ID NO. 2.

An expression vector comprising a nucleic acid sequence encoding a mammalian epsin 3 polypeptide is also considered within the scope of the invention as claimed. In a specific embodiment of the invention, such an expression vector may be characterized as comprising a nucleic acid sequence that encodes SEQ ID NO:2 or an expression vector comprising a nucleic acid sequence encoding at least 10, 20, 30, 40, 50, 80 or 100 contiguous amino acids of SEQ ID NO:2. An alternate embodiment may encompass an expression vector comprising the nucleic acid sequence as set forth in SEQ ID NO:1 or an expression vector comprising a nucleic acid sequence encoding at least 10, 20, 30, 40, 50, 80 or 100 contiguous bases of SEQ ID NO:1. It is further envisioned that the expression vector may comprise a virus and that the expression construct may include a promoter operably linked to the epsin 3-encoding nucleic acid sequence.

Another embodiment of the invention encompasses the use of epsin 3 protein or nucleic acid sequence encoding the epsin 3 protein to detect tissue damage, particularly epithelial damage. In an envisioned embodiment, this method entails detecting epithelial damage by screening for epsin 3. More particularly, the epithelial damage may be caused by cancer, or other pathologies exhibiting altered cell:extracellular matrix interactions. Such pathologies include, but are not limited to pyogenic granuloma, pyoderma gangrenosum, decubitus ulcers, venous-stasis ulcers, diabetic ulcers, poorly-healing wounds, burns, normal surgical invasions, oral lesions, muscosal lesions, airway/lung lesions, gastric ulcerations, intestinal ulcerations, ulcerative colitis, Chrohn's disease or opthalmic ulcerations.

Yet further, another embodiment encompasses a method of enhancing re-epithelialization comprising administering an epsin 3 protein or a functional equivalent thereof to the wound of an organism. An organism may include, but is not limited to humans, rats, mice, monkeys, dogs, cats or pigs. It is envisioned that overexpression or increased abundance of epsin 3 protein may enhance the migration of keratinocytes in pathologies that fail to heal or exhibit altered cell:extracelluar matrix interactions. Such pathologies include, but are not limited to pyogenic granuloma, pyoderma gangrenosum, decubitus ulcers, venous-stasis ulcers, diabetic ulcers, poorly-healing wounds, burns, normal surgical invasions, oral lesions, muscosal lesions, airway/lung lesions, gastric ulcerations, intestinal ulcerations, ulcerative colitis, Chrohn's disease or opthalmic ulcerations.

In further embodiments, the present invention provides a method of enhancing re-epithelialization comprising administering an expression vector to the wound of an organism, wherein the expression vector comprises a nucleic acid sequence encoding a mammalian epsin 3 polypeptide or functional equivalent thereof.

Another embodiment encompasses a method of inhibiting endocytosis and migration of cells comprising administering an inhibitor of epsin 3 to an organism. It is contemplated that inhibition of endocytosis or cell migration may prevent the invasiveness of cancerous cells. Yet further, it is contemplated that the inhibitor may be an antisense molecule, a ribozyme, an RNA interference molecule or an antibody.

It is also provided in the present invention a method of screening for a modulator of epsin 3 expression comprising: providing a cell expressing a epsin 3 polypeptide; contacting said cell with a candidate modulator; measuring epsin 3 expression; and comparing said epsin 3 expression in the presence of said candidate modulator with the expression of epsin 3 in the absence of said candidate modulator; wherein a difference in the expression of epsin 3 in the presence of said candidate modulator, as compared with the expression of epsin 3 in the absence of said candidate modulator, identifies said candidate modulator as a modulator of epsin 3 expression. It is envisioned that these modulators may be used to enhance or inhibit epsin 3 expression. Modulators that enhance epsin 3 expression may be used to promote more efficient wound healing or repair. Yet further, modulators that inhibit epsin 3 expression may be used to inhibit epsin 3 function, for example endocytosis or cell migration. It is contemplated that inhibition of epsin 3 may prevent the invasiveness of cancerous cells.

Yet further, it is also provided in the present invention a non-human transgenic animal comprising an expression cassette, wherein the expression vector comprises a nucleic acid sequence encoding a mammalian epsin 3 polypeptide or functional equivalent thereof and a promoter operable in eukaryotic cells, the promoter being heterologous to the epsin 3 polypeptide encoding region. The expression vector may further comprise a selectable marker. In specific embodiments, the promoter may be tissue specific, for example, an eptithelial tissue specific promoter. It is also contemplated that the promoter may be inducible. The non-human animal may be a mouse. In further aspects, a non-human transgenic animal may comprise a defective germ-line epsin 3 allele.

DESCRIPTION OF ILLUSTRATIVE EMBODIMENTS

The epsins are constitutively expressed genes that demonstrate a wide tissue distribution and are purported to provide a role in mediating the assembly and internalization of clathrin coated pits (Chen et al., 1998; Rosenthal et al., 1999). Originally identified by screening for proteins that interact with the EH (Eps15 homology) domains of Eps15 (Salcini et al., 1997; McPherson et al., 1998) and clathrin AP-2 (Wang et al., 1995), epsin functions as a molecular bridge to facilitate the ordered assembly of these molecules into the clathrin lattice at the plasma membrane. In addition, epsin contains two clathrin binding consensus sequences that have been shown to act cooperatively in clathrin interaction (Drake et al., 2000). Thus, epsin is a requisite for coordinating a specific molecular architecture prior to coated pit invagination. In fact, perturbation of epsin function in fibroblasts by over-expression or antibody injection potently inhibits this process (Chen et al., 1998; Rosenthal et al., 1999).

The present invention identifies a novel epsin, epsin 3, that retains the conserved structural features common to this gene family. Epsin 3 exhibits a significant degree of sequence identity when compared to other epsins and contains the ENTH protein module that is highly conserved from yeast to humans. Epsin 3 demonstrates greater sequence diversity distal to the ENTH domain, yet multiple DPW and three NPF motifs shown to be required for Eps15 and AP-2 binding (Chen et al., 1998; Rosenthal et al., 1999), respectively, are fully conserved.

Differential display RT-PCR (ddRT-PCR) was used to identify the novel gene, epsin 3, which is induced in keratinocytes following collagen contact. The entire coding sequence for human epsin 3 was amplified by RT-PCR from collagen-activated keratinocytes. Sequencing of the resulting cDNA and translation revealed an 1896 bp open reading frame that codes for a 632 amino acid protein. The nucleotide sequence data are in the GenBank nucleotide sequence database with the accession number AF324241.

Epsin 3 retains typical structural motifs and behavioral activity common to previously described epsins, however, it is profoundly divergent from other members of this gene family, as expression is limited to wounded or pathologic tissues with altered cell:extracellular matrix interactions, suggesting that epsin 3 may serve a role during repair of tissues that demonstrate a disrupted basement membrane. Furthermore, these finidings underscore the importance of the extracellular matrix in stimulating keratinocyte activation following cutaneous injury and suggest that common mechanisms may influence cell activation in other wounded or pathologic epithelial tissues.

I. Proteins, Polypeptides and Proteinaceous Compositions
   A. Epsin 3 Protein

The predicted epsin 3 protein sequence demonstrates an identical tripartite domain structure common to the epsin gene family. The region of highest similarity is the ENTH domain that, following alignment, reveals many regions of 100% conservation and 80–82% sequence identity overall. Although the DPW and NPF domains of epsin 3 possess significantly less sequence identity when compared to epsins 1 and 2 (11–28% and 28–34%, respectively), the three NPF motifs are 100% conserved. Furthermore, the DPW domain of epsin 3 contains 4 conserved (8 total) DPW motifs, which is consistent with the variability demonstrated among each family member.

The protein sequence for human epsin 3 is provided in SEQ ID NO:2. In addition to the entire epsin 3 molecule, the present invention also relates to fragments of the polypeptides that may or may not retain several of the functions described below. Fragments, including the N-terminus of the molecule, may be generated by genetic engineering of translation stop sites within the coding region (discussed below). Alternatively, treatment of the epsin 3 protein with proteolytic enzymes, known as proteases, can produces a variety of N-terminal, C-terminal and internal fragments. Polypeptides range from 6, 7, 8, 9, 10, 15, 20, 25, 30, 35, 40, 45, and 50 residues, such as those made synthetically, up to 100, 150, 200, 250, 300, 350, 400, 450, 500, 600 and more residues, which are conveniently produced by recombinant means or by proteolytic digestion of full length epsin 3.

In certain embodiments the size of the at least one proteinaceous molecule may comprise, but is not limited to, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700 or greater amino molecule residues, and any range derivable therein.

In certain embodiments, the present invention concerns novel compositions comprising at least one proteinaceous molecule, such as epsin 3 or a modulator of epsin 3, such as an antibody against epsin 3. One skilled in the art understands that "at least one proteinaceous molecule" as used herein comprises an epsin 3 protein, an epsin 3 polypeptide or a variant of an epsin 3 protein. Yet further, the proteinaceous compound may comprise a protein or a polypeptide that modulates epsin 3.

As used herein, a "proteinaceous molecule," "proteinaceous composition," "proteinaceous compound," "proteinaceous chain" or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" and "protein" or "peptide" terms described above may be used interchangeably herein.

As used herein, an "amino molecule" refers to any amino acid, amino acid derivative or amino acid mimic as would be known to one of ordinary skill in the art. In certain embodiments, the residues of the proteinaceous molecule are sequential or contiguous, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" or the protein or polypeptide of the present invention encompasses amino molecule sequences comprising at least one of the 20 common amino acids in naturally synthesized proteins, or at least one modified or unusual amino acid, including but not limited to those shown on Table 1 below.

TABLE 1

Modified and Unusual Amino Acids

| Abbr. | Amino Acid |
|---|---|
| Aad | 2-Aminoadipic acid |
| Baad | 3-Aminoadipic acid |
| Bala | β-alanine, β-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| Baib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| Ahyl | allo-Hydroxylysine |
| 3Hyp | 3-Hydroxyproline |
| 4Hyp | 4-Hydroxyproline |
| Ide | Isodesmosine |
| Aile | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

In further embodiments the proteinaceous composition comprises a biocompatible protein, polypeptide or peptide. As used herein, the term "biocompatible" refers to a substance, which produces no significant untoward effects when applied to, or administered to, a given organism according to the methods and amounts described herein. Such untoward or undesirable effects are those such as significant toxicity or adverse immunological reactions. In preferred embodiments, biocompatible protein, polypeptide or peptide containing compositions will generally be mammalian proteins or peptides or synthetic proteins or peptides each essentially free from toxins, pathogens and harmful immunogens.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases (http://www.ncbi.nlm.nih.gov/). The coding regions for these known genes may be amplified and/or expressed using the techniques disclosed herein or as would be known to those of ordinary skill in the art. Alternatively, various commercial preparations of proteins, polypeptides and peptides are known to those of skill in the art.

B. Variants of Epsin 3

Amino acid sequence variants of the epsin 3 polypeptides of the present invention can be substitutional, insertional or deletion variants. Deletion variants lack one or more residues of the native protein that are not essential for function or immunogenic activity. Another common type of deletion variant is one lacking signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids that are identical or functionally equivalent to the amino acids of an epsin 3 polypeptide or a modulator of an epsin 3 provided the biological activity of the protein is maintained.

The term "functionally equivalent codon" is used herein to refer to codons that encode the same amino acid, such as the six codons for arginine or serine, and also refers to codons that encode biologically equivalent amino acids (see Table 2, below).

TABLE 2

Codon Table

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity, as discussed below. Table 2 shows the codons that encode particular amino acids.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produces a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure. See e.g., Johnson (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principle outline above, to engineer second generation molecules having many of the natural properties of epsin 3 but with altered and even improved characteristics.

C. Fusion Proteins

A specialized kind of insertional variant is the fusion protein. It is contemplated that the entire epsin 3 protein or a fragment of the epsin 3 protein may be used to construct a fusion protein to enhance tissue specific or cell specific targeting of the epsin 3 protein.

A fusion protein generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes such as a hydrolase, glycosylation domains, cellular targeting signals or transmembrane regions.

D. Protein Purification

In specific embodiments, it may be desirable to purify epsin 3 proteins, polypeptides, peptides or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (e.g., alter pH, ionic strength, and temperature).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and Helix pomatia lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand also should provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

E. Synthetic Peptides

The present invention also describes smaller epsin-related peptides for use in various embodiments of the present invention. Because of their relatively small size, the peptides of the invention can also be synthesized in solution or on a solid support in accordance with conventional techniques. Various automatic synthesizers are commercially available and can be used in accordance with known protocols. See, for example, Stewart and Young (1984); Tarn et al. (1983); Merrifield (1986); and Barany and Merrifield (1979), each incorporated herein by reference. Short peptide sequences, or libraries of overlapping peptides, usually from about 6 up to about 100 amino acids or greater which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

F. Antibodies

Another embodiment of the present invention encompasses antibodies, in some cases, a human monoclonal antibody, immunoreactive with the polypeptide sequence of epsin 3 (SEQ ID NO:2). It is understood that antibodies can be used for inhibiting or modulating epsin 3. It is also understood that this antibody is useful for screening samples from human patients for the purpose of detecting the amount of epsin 3 protein present in the samples. The antibody may also be useful in the screening of expressed DNA segments or peptides and proteins for the discovery of related antigenic sequences. In addition, the antibody may be useful in passive immunotherapy for cancer. All such uses of the antibody and any antigens or epitopic sequences so discovered fall within the scope of the present invention.

1. Antibody Generation

Antibodies may be generated against full length epsin 3 protein. It is also contemplated that antibodies may be generated in response to smaller epsin 3 constructs comprising epitopic core regions, including wild-type epsin 3 or mutant epsin 3 epitopes.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

Monoclonal antibodies (mAbs) are recognized to have certain advantages, e.g., reproducibility and large-scale production, and their use is generally preferred. The invention thus provides monoclonal antibodies of the human, murine, monkey, rat, hamster, rabbit and even chicken origin.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like.

The techniques for preparing and using various antibody-based constructs and fragments are well known in the art. Means for preparing and characterizing antibodies are also well known in the art (See, e.g., Harlow and Lane, "Antibodies: A Laboratory Manual," Cold Spring Harbor Laboratory, 1988; incorporated herein by reference).

A polyclonal antibody may be prepared by immunizing an animal with an immunogenic polypeptide composition in accordance with the present invention and collecting antisera from that immunized animal. A wide range of animal species can be used for the production of antisera. Typically the animal used for production of antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin also can be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

As also well known in the art, the immunogenicity of a particular immunogen composition can be enhanced by the use of non-specific stimulators of the immune response, known as adjuvants. Suitable molecule adjuvants include all acceptable immunostimulatory compounds, such as cytokines, toxins or synthetic compositions.

Adjuvants that may be used include IL-1, IL-2, IL-4, IL-7, IL-12, γ-interferon, GMCSF, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion also is contemplated. MHC antigens may even be used. Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/m$^2$) (Johnson/Mead, NJ), cytokines such as γ-interferon, IL-2, or IL-12 or genes encoding proteins involved in immune helper functions, such as B-7.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization.

A second, booster injection may also be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. The methods for generating monoclonal antibodies generally begin along the same lines as those for preparing polyclonal antibodies. Rodents such as mice and rats are preferred animals, however, the use of rabbit, sheep or frog cells is also possible. The use of rats may provide certain advantages (Goding, 1986), but mice are preferred, with the BALB/c mouse being most preferred as this is most routinely used and generally gives a higher percentage of stable fusions.

The animals are injected with antigen, generally as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible.

Often, a panel of animals will have been immunized and the spleen of an animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding, 1986).

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. First, a sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide mAbs in high concentration. Second, the individual cell lines could be cultured in vitro, where the mAbs are naturally secreted into the culture medium from which they can be readily obtained in high concentrations.

mAbs may be further purified, if desired, using filtration, centrifugation and various chromatographic methods such as HPLC or affinity chromatography. Fragments of the monoclonal antibodies of the invention can be obtained from the monoclonal antibodies so produced by methods, which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It also is contemplated that a molecular cloning approach may be used to generate mAbs. For this, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Humanized monoclonal antibodies are antibodies of animal origin that have been modified using genetic engineering techniques to replace constant region and/or variable region framework sequences with human sequences, while retaining the original antigen specificity. Such antibodies are commonly derived from rodent antibodies with specificity against human antigens. Such antibodies are generally useful for in vivo therapeutic applications. This strategy reduces the host response to the foreign antibody and allows selection of the human effector functions.

"Humanized" antibodies are also contemplated, as are chimeric antibodies from mouse, rat, or other species, bearing human constant and/or variable region domains, bispecific antibodies, recombinant and engineered antibodies and fragments thereof. The techniques for producing humanized immunoglobulins are well known to those of skill in the art. For example U.S. Pat. No. 5,693,762 discloses methods for producing, and compositions of, humanized immunoglobulins having one or more complementarity determining regions (CDR's). When combined into an intact antibody, the humanized immunoglobulins are substantially non-immunogenic in humans and retain substantially the same affinity as the donor immunoglobulin to the antigen, such as a protein or other compound containing an epitope. Examples of other teachings in this area include U.S. Pat. Nos. 6,054,297; 5,861,155; and 6,020,192, all specifically incorporated by reference. Methods for the development of antibodies that are "custom-tailored" to the patient's disease are likewise known and such custom-tailored antibodies are also contemplated.

2. Immunodetection Methods

As discussed, in some embodiments, the present invention concerns immunodetection methods for binding, purifying, removing, quantifying and/or otherwise detecting biological components such as antigenic regions on polypeptides and peptides. The immunodetection methods of the present invention can be used to identify antigenic regions of a peptide, polypeptide, or protein that has therapeutic implications, particularly in reducing the immunogenicity or antigenicity of the peptide, polypeptide, or protein in a target subject.

In specific embodiments, immunodetection methods may be used to quantify epsin 3 expression as a marker for tissues undergoing repair. It is also envisioned that immunodetection methods using epsin 3 may provide a diagnostic tool by which invasion of cancerous tissue can be measured.

Immunodetection methods include enzyme linked immunosorbent assay (ELISA), radioimmunoassay (RIA), immunoradiometric assay, fluoroimmunoassay, chemiluminescent assay, bioluminescent assay, Western blot, and immunohistochemistry though several others are well known to those of ordinary skill. The steps of various useful immunodetection methods have been described in the scientific literature, such as, e.g., Doolittle et al., 1999; Gulbis et al., 1993; De Jager et al., 1993; and Nakamura et al., 1987, each incorporated herein by reference.

In general, the immunobinding methods include obtaining a sample suspected of containing a protein, polypeptide and/or peptide, and contacting the sample with a first antibody, monoclonal or polyclonal, in accordance with the present invention, as the case may be, under conditions effective to allow the formation of immunocomplexes.

These methods include methods for purifying a protein, polypeptide and/or peptide from organelle, cell, tissue or organism's samples. In these instances, the antibody removes the antigenic protein, polypeptide and/or peptide component from a sample. The antibody will preferably be linked to a solid support, such as in the form of a column matrix, and the sample suspected of containing the protein, polypeptide and/or peptide antigenic component will be applied to the immobilized antibody. The unwanted components will be washed from the column, leaving the antigen immunocomplexed to the immobilized antibody to be eluted.

The immunobinding methods also include methods for detecting and quantifying the amount of an antigen component in a sample and the detection and quantification of any immune complexes formed during the binding process. Here, one would obtain a sample suspected of containing an antigen or antigenic domain, and contact the sample with an antibody against the antigen or antigenic domain, and then detect and quantify the amount of immune complexes formed under the specific conditions.

In terms of antigen detection, the biological sample analyzed may be any sample that is suspected of containing an epsin 3 antigen or antigenic domain, such as, for example, a tissue section or specimen, a homogenized tissue extract, a cell, an organelle, separated and/or purified forms of any of the above antigen-containing compositions, or even any biological fluid that comes into contact with the cell or tissue, including blood and/or serum.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any epsin 3 antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939, 350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

Yet further, another method of immunodection is immunohistochemistry. It is contemplated that the antibodies of the present invention may also be used in conjunction with both fresh-frozen and/or formalin-fixed, paraffin-embedded tissue blocks prepared for study by immunohistochemistry (IHC). For example, immunohistochemistry may be utilized to characterize epsin 3 or to evaluate the amount epsin 3 expression in a tissue. The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990).

Briefly, frozen-sections may be prepared by rehydrating 50 mg of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25–50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

3. Antibody Conjugates

The present invention further provides antibodies against epsin 3, generally of the monoclonal type, that are linked to one or more other agents to form an antibody conjugate. Any antibody of sufficient selectivity, specificity and affinity may be employed as the basis for an antibody conjugate. Such properties may be evaluated using conventional immunological screening methodology known to those of skill in the art.

Certain examples of antibody conjugates are those conjugates in which the antibody is linked to a detectable label. "Detectable labels" are compounds or elements that can be detected due to their specific functional properties, or chemical characteristics, the use of which allows the antibody to which they are attached to be detected, and further quantified if desired. Another such example is the formation of a conjugate comprising an antibody linked to a cytotoxic or anti-cellular agent, as may be termed "immunotoxins" (described in U.S. Pat. Nos. 5,686,072, 5,578,706, 4,792,447, 5,045,451, 4,664,911 and 5,767,072, each incorporated herein by reference).

Antibody conjugates are thus preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Again, antibody-directed imaging is less preferred for use with this invention.

Many appropriate imaging agents are known in the art, as are methods for their attachment to antibodies (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the antibody (U.S. Pat. No. 4,472,509). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper 67, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and yttrium$^{90}$. $^{125}$I is often being preferred for use in certain embodiments, and technicium$^{99m}$ and indium$^{111}$ are also often preferred due to their low energy and suitability for long range detection.

Radioactively labeled monoclonal antibodies of the present invention may be produced according to well-known methods in the art. For instance, monoclonal antibodies can be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with technetium-$^{99m}$ by ligand exchange process, for example, by reducing pertechnate with stannous solution, chelating the reduced technetium onto a Sephadex column and applying the antibody to this column or by direct labeling techniques, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetri-aminepentaacetic acid (DTPA) and ethylene diaminetetraceticc acid (EDTA). Also contemplated for use are fluorescent labels, including rhodamine, fluorescein isothiocyanate and renographin.

The much preferred antibody conjugates of the present invention are those intended primarily for use in vitro, where the antibody is linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference.

II. Nucleic Acid Molecules

A. Polynucleotides Encoding Native Proteins or Modified Proteins

The present invention concerns nucleic acids or polynucleotides, isolatable from cells, that are free from total genomic DNA and that are capable of expressing all or part of an epsin 3 protein or polypeptide. Recombinant proteins can be purified from expressing cells to yield active proteins.

As used herein, the term "DNA segment" refers to a DNA molecule that has been isolated free of total genomic DNA of a particular species. Therefore, a DNA segment encoding a polypeptide refers to a DNA segment that contains wild-type, polymorphic, or mutant polypeptide-coding sequences yet is isolated away from, or purified free from, total mammalian or human genomic DNA. Included within the term "DNA segment" are a polypeptide or polypeptides, DNA segments smaller than a polypeptide, and recombinant vectors, including, for example, plasmids, cosmids, phage, viruses, and the like.

As used in this application, the term "epsin 3 polynucleotide" refers to an epsin 3-encoding nucleic acid molecule that has been isolated free of total genomic nucleic acid. Therefore, a "polynucleotide encoding epsin 3" refers to a DNA segment that contains wild-type (SEQ ID NO:1), mutant, or polymorphic epsin 3 polypeptide-coding sequences isolated away from, or purified free from, total mammalian or human genomic DNA. Therefore, for example, when the present application refers to the function or activity of epsin 3 or a "epsin 3 polypeptide," it is meant that the polynucleotide encodes a molecule that has the activity of epsin 3.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

Similarly, a polynucleotide comprising an isolated or purified wild-type, polymorphic, or mutant polypeptide gene refers to a DNA segment including wild-type, polymorphic, or mutant polypeptide coding sequences and, in certain aspects, regulatory sequences, isolated substantially away from other naturally occurring genes or protein encoding sequences. In this respect, the term "gene" is used for simplicity to refer to a functional protein, polypeptide, or peptide-encoding unit. As will be understood by those in the art, this functional term includes genomic sequences, cDNA sequences, and smaller engineered gene segments that express, or may be adapted to express, proteins, polypeptides, domains, peptides, fusion proteins, and mutants.

In a non-limiting example, one or more nucleic acid constructs may be prepared that include a contiguous stretch of nucleotides identical to or complementary to the epsin 3 gene (SEQ ID NO:1). A nucleic acid construct may be at least 10, 20, 30, 40, 50, 60, 70, 80, 90, 100, 110, 120, 130, 140, 150, 160, 170, 180, 190, 200, 250, 300, 400, 500, 600, 700, 800, 900, 1,000, 2,000, 3,000, 4,000, 5,000 nucleotides in length, as well as constructs of greater size, up to and including chromosomal sizes (including all intermediate lengths and intermediate ranges), given the advent of nucleic acid constructs such as a yeast artificial chromosome are known to those of ordinary skill in the art. It will be readily understood that "intermediate lengths" and "intermediate ranges," as used herein, means any length or range including or between the quoted values (i.e., all integers including and between such values). For example, it will be readily understood that "intermediate lengths", in these contexts, means any length between the quoted ranges, such as 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 105, 110, 115, 120, 130, 140, 150, 160, 170, 180, 190, including all integers through the 200–500; 500–1,000; 1,000–2,000; 2,000–3,000; 3,000–5,000; 5,000–10,000 ranges, up to and including sequences of about 12,001, 12,002, 13,001, 13,002, 15,000, 20,000 and the like.

It is also contemplated that the nucleic acid constructs of the present invention may encode full-length epsin 3 polypeptide from any source or encode a truncated version of the epsin 3 polypeptide, such that the transcript of the coding region represents the truncated version. The truncated transcript may then be translated into a truncated protein. Alternatively, a nucleic acid sequence may encode a full-length epsin 3 polypeptide sequence or variant thereof with additional heterologous coding sequences, for example to allow for purification of the polypeptide, transport, secretion, post-translational modification, or for therapeutic benefits such as targeting or efficacy. A tag or other heterologous polypeptide may be added to the modified polypeptide-encoding sequence, wherein "heterologous" refers to a polypeptide that is not the same as the modified polypeptide.

The DNA segments used in the present invention encompass biologically functional equivalent modified polypeptides and peptides. Such sequences may arise as a consequence of codon redundancy and functional equivalency that are known to occur naturally within nucleic acid sequences and the proteins thus encoded. Yet further, one skilled in the art understands that a particular polypeptide from a given species may be represented by natural variants that have slightly different nucleic acid sequences but, nonetheless, encode the same protein. Alternatively, functionally equivalent proteins or peptides may be created via the application of recombinant DNA technology, in which changes in the protein structure may be engineered, based on considerations of the properties of the amino acids being exchanged. Changes designed by human may be introduced through the application of site-directed mutagenesis techniques, e.g., to introduce improvements to the antigenicity of the protein, to reduce toxicity effects of the protein in vivo to a subject given the protein, or to increase the efficacy of any treatment involving the protein.

It also will be understood that this invention is not limited to the particular nucleic acid and amino acid sequences of SEQ ID NO:1 or SEQ ID NO:2. Recombinant vectors and isolated DNA segments may therefore variously include the epsin 3 coding regions themselves, coding regions bearing selected alterations or modifications in the basic coding region, or they may encode larger polypeptides that nevertheless include epsin 3-coding regions or may encode biologically functional equivalent proteins or peptides that have variant amino acids sequences.

1. Vectors

The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

In certain embodiments, the invention concerns isolated DNA segments and recombinant vectors that include within their sequence a contiguous nucleic acid sequence from that shown in SEQ ID NO:1. This definition is used in the same sense as described above and means that the nucleic acid sequence substantially corresponds to a contiguous portion of that shown in SEQ ID NO:1 and has relatively few codons that are not identical, or functionally equivalent, to the codons of SEQ ID NO:1.

In particular embodiments, the invention concerns isolated DNA segments and recombinant vectors incorporating DNA sequences that encode a wild-type, polymorphic, or mutant epsin 3 polypeptide or peptide that includes within its amino acid sequence a contiguous amino acid sequence in accordance with, or essentially corresponding to a native polypeptide. The term "recombinant" may be used in conjunction with a polypeptide or the name of a specific polypeptide, and this generally refers to a polypeptide produced from a nucleic acid molecule that has been manipulated in vitro or that is the replicated product of such a molecule.

Native and modified polypeptides may be encoded by a nucleic acid molecule comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., (1989) and Ausubel et al., 1996, both incorporated herein by reference. In addition to encoding a modified polypeptide such as modified gelonin, a vector may encode non-modified polypeptide sequences such as a tag or targetting molecule. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage. A targetting molecule is one that directs the modified polypeptide to a particular organ, tissue, cell, or other location in a subject's body.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

a. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it may be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Table 3 lists several elements/promoters that may be employed, in the context of the present invention, to regulate the expression of a gene. This list is not intended to be exhaustive of all the possible elements involved in the promotion of expression but, merely, to be exemplary thereof. Table 4 provides examples of inducible elements, which are regions of a nucleic acid sequence that can be activated in response to a specific stimulus.

TABLE 3

| Promoter/Enhancer | |
|---|---|
| Promoter/Enhancer | References |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-Dra | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell et al., 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |
| Papilloma Virus | Campo et al., 1983; Lusky et al., 1983; Spandidos and Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 4

Inducible Elements

| Element | Inducer | References |
| --- | --- | --- |
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al, 1997), insulin-like growth factor II (Wu et al., 1997), human platelet endothelial cell adhesion molecule-1 (Almendro et al., 1996).

In specific aspects of the present invention, a tissue-specific promoter is a promoter that can direct expression to specific epithelial compartments, for example, but not limted to Keratin-14, which directs expression to basal keratinocytes, Keratin-10, which directs expression to suprabasal keratinocytes, and Keatin-6 or Keratin-16, which directs expression to migrating keratinocytes. It is also contmeplated that other tissue-specific promoters may be used, such as colon epithelium or transformed or invasive cancer specific promoters.

Also contemplated as useful in the present invention are epsin specific or epsin 3 specific promoters. Additional viral promoters, cellular promoters/enhancers and inducible promoters/enhancers that could be used in combination with the present invention are listed in Tables 3 and 4. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest. Alternatively, a tissue-specific promoter for cancer gene therapy or the targeting of tumors may be employed with the nucleic acid molecules of the present invention.

b. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5'-methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

c. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, incorporated herein by reference.)

e. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

f. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

g. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

h. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

2. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid, such as a modified protein-encoding sequence, is transferred or introduced into the host cell. A transformed cell includes the primary subject cell and its progeny.

Host cells may be derived from prokaryotes or eukaryotes, including yeast cells, insect cells, and mammalian cells, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla, Calif.). Alternatively, bacterial cells such as *E. coli* LE392 could be used as host cells for phage viruses. Appropriate yeast cells include *Saccharomyces cerevisiae*, *Saccharomyces pombe*, and *Pichia pastoris*.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

3. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

B. Antisense and Ribozymes

Antisense, ribozyme, and double-stranded RNA molecules target a particular sequence to achieve a reduction or elimination of a particular polypeptide, such as epsin 3. Thus, it is contemplated that nucleic acid molecules that are identical or complementary to all or part of SEQ ID NO: 1 are included as part of the invention.

1. Antisense Molecules

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNAs, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs may include regions complementary to intron/exon splice junctions. Thus, antisense constructs with complementarity to regions within 50–200 bases of an intron-exon splice junction may be used. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

2. Ribozymes

The use of epsin 3-specific ribozymes is claimed in the present application. The following information is provided in order to compliment the earlier section and to assist those of skill in the art in this endeavor.

Ribozymes are RNA-protein complexes that cleave nucleic acids in a site-specific fashion. Ribozymes have specific catalytic domains that possess endonuclease activity (Kim and Cech, 1987; Gerlack et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990; Sioud et al., 1992). Recently, it was reported that ribozymes elicited genetic changes in some cell lines to which they were applied; the altered genes included the oncogenes H-ras, c-fos and genes of HIV. Most of this work involved the modification of a target mRNA, based on a specific mutant codon that is cleaved by a specific ribozyme. In light of the information included herein and the knowledge of one of ordinary skill in the art, the preparation and use of additional ribozymes that are specifically targeted to a given gene will now be straightforward.

Several different ribozyme motifs have been described with RNA cleavage activity (reviewed in Symons, 1992). Examples that would be expected to function equivalently for the down regulation of epsin 3 include sequences from the Group I self splicing introns including tobacco ringspot virus (Prody et al., 1986), avocado sunblotch viroid (Palukaitis et al., 1979; Symons, 1981), and Lucerne transient streak virus (Forster and Symons, 1987). Sequences from these and related viruses are referred to as hammerhead ribozymes based on a predicted folded secondary structure.

Other suitable ribozymes include sequences from RNase P with RNA cleavage activity (Yuan et al., 1992; Yuan and Altman, 1994), hairpin ribozyme structures (Berzal-Herranz et al., 1992; Chowrira et al., 1993) and hepatitis δ virus based ribozymes (Perrotta and Been, 1992). The general design and optimization of ribozyme directed RNA cleavage activity has been discussed in detail (Haseloff and Gerlach, 1988; Symons, 1992; Chowrira, et al., 1994; and Thompson, et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozymes, the cleavage site is a dinucleotide sequence on the target RNA, uracil (U) followed by either an adenine, cytosine or uracil (A,C or U; Perriman, et al., 1992; Thompson, et al., 1995). The frequency of this dinucleotide occurring in any given RNA is statistically 3 out of 16. Therefore, for a given target messenger RNA of 1000 bases, 187 dinucleotide cleavage sites are statistically possible. The message for IGFBP-2 targeted here are greater than 1400 bases long, with greater than 260 possible cleavage sites.

Designing and testing ribozymes for efficient cleavage of a target RNA is a process well known to those skilled in the art. Examples of scientific methods for designing and testing ribozymes are described by Chowrira et al. (1994) and Lieber and Strauss (1995), each incorporated by reference. The identification of operative and preferred sequences for use in epsin 3-targeted ribozymes is simply a matter of preparing and testing a given sequence, and is a routinely practiced "screening" method known to those of skill in the art.

3. RNA Interference

It is also contemplated in the present invention that double-stranded RNA may be used as an interference molecule, e.g., RNA interference (iRNA).

RNA intereference is used to "knock out" or inhibit a particular gene of interest by simply injecting, bathing or feeding to the organsim of interest bacteria expressing a double-stranded RNA molecule. This technique selectively "knock outs" gene function without requring transfection or recombinant techniques (Giet, 2001; Hammond, 2001).

Thus, in certain embodiments, double-stranded epsin 3 RNA may be synthesized or produced using standard molecular technqiues described herein.

C. Nucleic Acid Detection

In addition to their use in directing the expression of epsin 3, polypeptides and/or peptides, the nucleic acid sequences disclosed herein have a variety of other uses. For example, they have utility as probes or primers for embodiments involving nucleic acid hybridization. They may be used in diagnostic or screening methods of the present invention. Detection of nucleic acids encoding epsin 3 are encompassed by the invention.

The various probes and primers designed around the nucleotide sequences of the present invention may be of any length. By assigning numeric values to a sequence, for example, the first residue is 1, the second residue is 2, etc., an algorithm defining all primers can be proposed:

n to n+y where n is an integer from 1 to the last number of the sequence and y is the length of the primer minus one, where n+y does not exceed the last number of the sequence. Thus, for a 10-mer, the probes correspond to bases 1 to 10, 2 to 11, 3 to 12 . . . and so on. For a 15-mer, the probes correspond to bases 1 to 15, 2 to 16, 3 to 17 . . . and so on. For a 20-mer, the probes correspond to bases 1 to 20, 2 to 21, 3 to 22 . . . and so on.

1. Hybridization

The use of a probe or primer of between 13 and 100 nucleotides, preferably between 17 and 100 nucleotides in length, or in some aspects of the invention up to 1–2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, site-directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

2. Amplification of Nucleic Acids

Nucleic acids used as a template for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to SEQ ID NO:1 are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641.

Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990; Ohara et al., 1989).

3. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 1989). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

4. Other Assays

Other methods for genetic screening may be used within the scope of the present invention, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substititution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

a. Design and Theoretical Considerations for Relative Quantitative RT-PCR

Reverse transcription (RT) of RNA to cDNA followed by relative quantitative PCR (RT-PCR) can be used to determine the relative concentrations of specific mRNA species isolated from a cell, such as an epsin 3-encoding transcript. By determining that the concentration of a specific mRNA species varies, it is shown that the gene encoding the specific mRNA species is differentially expressed.

In PCR, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR amplification is directly proportional to the starting concentration of the target before the reaction began. By determining the concentration of the amplified products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR products and the relative mRNA abundances is only true in the linear range of the PCR reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR for a collection of RNA populations is that the concentrations of the amplified PCR products must be sampled when the PCR reactions are in the linear portion of their curves.

The second condition that must be met for an RT-PCR experiment to successfully determine the relative abundances of a particular mRNA species is that relative concentrations of the amplifiable cDNAs must be normalized to some independent standard. The goal of an RT-PCR experiment is to determine the abundance of a particular mRNA species relative to the average abundance of all mRNA species in the sample.

Most protocols for competitive PCR utilize internal PCR standards that are approximately as abundant as the target. These strategies are effective if the products of the PCR amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR assay for plant tissue. The problems inherent in plant tissue samples are that they are of variable quantity (making normalization problematic), and that they are of variable quality (necessitating the co-amplification of a reliable internal control, preferably of larger size than the target). Both of these problems are overcome if the RT-PCR is performed as a relative quantitative RT-PCR with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other studies may be performed using a more conventional relative quantitative RT-PCR assay with an external standard protocol. These assays sample the PCR products in the linear portion of their amplification curves. The number of PCR cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR assays can be superior to those derived from the relative quantitative RT-PCR assay with an internal standard.

One reason for this advantage is that without the internal standard/competitor, all of the reagents can be converted into a single PCR product in the linear range of the amplification curve, thus increasing the sensitivity of the assay. Another reason is that with only one PCR product, display of the product on an electrophoretic gel or another display method becomes less complex, has less background and is easier to interpret.

b. Chip Technologies

Specifically contemplated by the present inventors are chip-based DNA technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization (see also, Pease et al., 1994; and Fodor et al, 1991). It is contemplated that this technology may be used in conjunction with evaluating the expression level of epsin 3 with respect to diagnostic, as well as preventative and treatment methods of the invention.

III. Mutagenesis

In the design of proteins and polypeptides of the present invention, it may be necessary to utilize standard mutagenesis techniques. Mutagenesis may be used to screen for variants, mutants or analogs of epsin 3 proteins or peptides or modulators of epsin 3.

A. Chemical Mutagenesis

Chemical mutagenesis offers certain advantages, such as the ability to find a full range of mutant alleles with degrees of phenotypic severity, and is facile and inexpensive to perform. The majority of chemical carcinogens produce mutations in DNA. Benzo[a]pyrene, N-acetoxy-2-acetyl aminofluorene and aflotoxin B1 cause GC to TA transversions in bacteria and mammalian cells. Benzo[a]pyrene also can produce base substitutions such as AT to TA. N-nitroso compounds produce GC to AT transitions. Alkylation of the O4 position of thymine induced by exposure to n-nitrosoureas results in TA to CG transitions.

B. In vitro Scanning Mutagenesis

Random mutagenesis also may be introduced using error prone PCR (Cadwell and Joyce, 1992). The rate of mutagenesis may be increased by performing PCR in multiple tubes with dilutions of templates.

One particularly useful mutagenesis technique is alanine scanning mutagenesis in which a number of residues are substituted individually with the amino acid alanine so that the effects of losing side-chain interactions can be determined, while minimizing the risk of large-scale perturbations in protein conformation (Cunningham et al., 1989).

In recent years, techniques for estimating the equilibrium constant for ligand binding using minuscule amounts of protein have been developed (Blackburn et al., 1991; U.S. Pat. Nos. 5,221,605 and 5,238,808). The ability to perform functional assays with small amounts of material can be exploited to develop highly efficient, in vitro methodologies for the saturation mutagenesis of antibodies. The inventors bypassed cloning steps by combining PCR mutagenesis with coupled in vitro transcription/translation for the high throughput generation of protein mutants. Here, the PCR products are used directly as the template for the in vitro transcription/translation of the mutant single chain antibodies. Because of the high efficiency with which all 19 amino acid substitutions can be generated and analyzed in this way, it is now possible to perform saturation mutagenesis on numerous residues of interest, a process that can be described as in vitro scanning saturation mutagenesis (Burks et al., 1997).

In vitro scanning saturation mutagenesis provides a rapid method for obtaining a large amount of structure-function information including: (i) identification of residues that modulate ligand binding specificity, (ii) a better understanding of ligand binding based on the identification of those amino acids that retain activity and those that abolish activity at a given location, (iii) an evaluation of the overall plasticity of an active site or protein subdomain, (iv) identification of amino acid substitutions that result in increased binding.

C. Random Mutagenesis by Fragmentation and Reassembly

A method for generating libraries of displayed polypeptides is described in U.S. Pat. No. 5,380,721. The method comprises obtaining polynucleotide library members, pooling and fragmenting the polynucleotides, and reforming fragments therefrom, performing PCR amplification, thereby homologously recombining the fragments to form a shuffled pool of recombined polynucleotides.

D. Site-Directed Mutagenesis

Structure-guided site-specific mutagenesis represents a powerful tool for the dissection and engineering of protein-ligand interactions (Wells, 1996; Braisted et al, 1996). The technique provides for the preparation and testing of sequence variants by introducing one or more nucleotide sequence changes into a selected DNA.

Site-specific mutagenesis uses specific oligonucleotide sequences which encode the DNA sequence of the desired mutation, as well as a sufficient number of adjacent, unmodified nucleotides. In this way, a primer sequence is provided with sufficient size and complexity to form a stable duplex on both sides of the deletion junction being traversed. A primer of about 17 to 25 nucleotides in length is preferred, with about 5 to 10 residues on both sides of the junction of the sequence being altered.

The technique typically employs a bacteriophage vector that exists in both a single-stranded and double-stranded form. Vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridization conditions. The hybridized product is subjected to DNA polymerizing enzymes such as *E. coli* polymerase I (Klenow fragment) in order to complete the synthesis of the mutation-bearing strand. Thus, a heteroduplex is formed, wherein one strand encodes the original non-mutated sequence, and the second strand bears the desired mutation. This heteroduplex vector is then used to transform appropriate host cells, such as *E. coli* cells, and clones are selected that include recombinant vectors bearing the mutated sequence arrangement.

Comprehensive information on the functional significance and information content of a given residue of protein can best be obtained by saturation mutagenesis in which all 19 amino acid substitutions are examined. The shortcoming of this approach is that the logistics of multiresidue saturation mutagenesis are daunting (Warren et al., 1996, Brown et al., 1996; Zeng et al., 1996; Burton and Barbas, 1994; Yelton et al., 1995; Jackson et al., 1995; Short et al., 1995; Wong et al., 1996; Hilton et al., 1996). Hundreds, and possibly even thousands, of site specific mutants must be studied. However, improved techniques make production and rapid screening of mutants much more straightforward. See also, U.S. Pat. Nos. 5,798,208 and 5,830,650, for a description of "walk-through" mutagenesis.

Other methods of site-directed mutagenesis are disclosed in U.S. Pat. Nos. 5,220,007; 5,284,760; 5,354,670; 5,366,878; 5,389,514; 5,635,377; and 5,789,166.

IV. Methods of Gene Transfer

In order to mediate the effect transgene expression in a cell, it will be necessary to transfer the therapeutic expression constructs of the present invention into a cell. Such transfer may employ viral or non-viral methods of gene transfer. This section provides a discussion of methods and compositions of gene transfer.

A. Viral Vector-Mediated Transfer

In certain embodiments, the nucleic acid sequence is incorporated into a viral particle to mediate gene transfer to a cell. Typically, the virus simply will be exposed to the appropriate host cell under physiologic conditions, permitting uptake of the virus. The present methods may be advantageously employed using a variety of viral vectors, as discussed below.

1. Adenovirus

Adenovirus is particularly suitable for use as a gene transfer vector because of its mid-sized DNA genome, ease of manipulation, high titer, wide target-cell range, and high infectivity. The roughly 36 kB viral genome is bounded by 100–200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence which makes them preferred mRNAs for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. The two goals are, to an extent, coterminous in that elimination of adenoviral genes serves both ends. By practice of the present invention, it is possible achieve both these goals while retaining the ability to manipulate the therapeutic constructs with relative ease.

The large displacement of DNA is possible because the cis elements required for viral DNA replication all are localized in the inverted terminal repeats (ITR) (100–200 bp) at either end of the linear viral genome. Plasmids containing ITR's can replicate in the presence of a non-defective adenovirus (Hay et al., 1984). Therefore, inclusion of these elements in an adenoviral vector should permit replication.

In addition, the packaging signal for viral encapsidation is localized between 194–385 bp (0.5–1.1 map units) at the left end of the viral genome (Hearing et al., 1987). This signal mimics the protein recognition site in bacteriophage λ DNA where a specific sequence close to the left end, but outside the cohesive end sequence, mediates the binding to proteins that are required for insertion of the DNA into the head structure. E1 substitution vectors of Ad have demonstrated that a 450 bp (0–1.25 map units) fragment at the left end of the viral genome could direct packaging in 293 cells (Levrero et al., 1991).

Previously, it has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus, an additional element was needed that would add specificity to the replication and/or packaging of the replication-deficient vector. That element, as provided for in the present invention, derives from the packaging function of adenovirus.

It has been shown that a packaging signal for adenovirus exists in the left end of the conventional adenovirus map (Tibbetts, 1977). Later studies showed that a mutant with a deletion in the E1A (194–358 bp) region of the genome grew poorly even in a cell line that complemented the early (E1A) function (Hearing and Shenk, 1983). When a compensating adenoviral DNA (0–353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved towards the interior of the Ad5 DNA molecule (Hearing et al., 1987).

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals are packaged selectively when compared to the helpers. If the preference is great enough, stocks approaching homogeneity should be achieved.

2. Retrovirus

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed Ψ, functions as a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990).

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and Ψ components is constructed (Mann et al., 1983). When a recombinant plasmid containing a human cDNA, together with the retroviral LTR and Ψ sequences is introduced into this cell line (by calcium phosphate precipitation for example), the Ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is collected, optionally concentrated, and used for gene transfer. Retroviral vectors are able to infect a broad variety of cell types. However, integration and stable expression of many types of retroviruses require the division of host cells (Paskind et al., 1975).

An approach designed to allow specific targeting of retrovirus vectors recently was developed based on the chemical modification of a retrovirus by the chemical addition of galactose residues to the viral envelope. This modification could permit the specific infection of cells such as hepatocytes via asialoglycoprotein receptors, should this be desired.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, the infection of a variety of human cells that bore those surface antigens was demonstrated with an ecotropic virus in vitro (Roux et al., 1989).

3. Adeno-Associated Virus

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42–46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

The terminal repeats of the AAV vector can be obtained by restriction endonuclease digestion of AAV or a plasmid such as p201, which contains a modified AAV genome (Samulski et al., 1987), or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e., stable and site-specific integration. The ordinarily skilled artisan also can determine which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo (Carter and Flotte, 1996; Chatterjee et al., 1995; Ferrari et al., 1996; Fisher et al., 1996; Flotte et al., 1993; Goodman et al., 1994; Kaplitt et al., 1994; 1996, Kessler et al., 1996; Koeberl et al., 1997; Mizukami et al., 1996).

AAV-mediated efficient gene transfer and expression in the lung has led to clinical trials for the treatment of cystic fibrosis (Carter and Flotte, 1995; Flotte et al, 1993). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., 1996; Flotte et al., 1993; Kaplitt et al., 1994; 1996; Koeberl et al., 1997; McCown et al., 1996; Ping et al., 1996; Xiao et al., 1996).

4. Other Viral Vectors

Other viral vectors may be employed as expression constructs in the present invention. Vectors derived from viruses such as vaccinia virus (Ridgeway, 1988; Baichwal and Sugden, 1986; Coupar et al., 1988) canary pox virus, herpes viruses, and lentivirus may be employed. These viruses offer several features for use in gene transfer into various mammalian cells.

B. Non-Viral Transfer

Several non-viral methods for the transfer of expression constructs into cultured mammalian cells are contemplated by the present invention. These include calcium phosphate precipitation (Graham & Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland & Weintraub, 1985), DNA-loaded liposomes (Nicolau & Sene, 1982; Fraley et al., 1979), cell sonication (Fechheimer et al., 1987), gene bombardment using high velocity microprojectiles (Yang et al., 1990), and receptor-mediated transfection (Wu & Wu, 1987; Wu & Wu, 1988).

Once the construct has been delivered into the cell the nucleic acid encoding the therapeutic gene may be positioned and expressed at different sites. In certain embodiments, the nucleic acid encoding the therapeutic gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In a particular embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh & Bachhawat, 1991). The addition of DNA to cationic liposomes causes a topological transition from liposomes to optically birefringent liquid-crystalline condensed globules (Radler et al., 1997). These DNA-lipid complexes are potential non-viral vectors for use in gene therapy.

Liposome-mediated nucleic acid delivery and expression of foreign DNA in vitro has been very successful. Using the β-lactamase gene, Wong et al., (1980) demonstrated the feasibility of liposome-mediated delivery and expression of foreign DNA in cultured chick embryo, HeLa, and hepatoma cells. Nicolau et al., (1987) accomplished successful liposome-mediated gene transfer in rats after intravenous injection. Also included are various commercial approaches involving "lipofection" technology.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear nonhistone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems which can be employed to deliver a nucleic acid encoding a therapeutic gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu & Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu & Wu, 1987) and transferring (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a cell type such as prostate, epithelial or tumor cells, by any number of receptor-ligand systems with or without liposomes. For example, the human prostate-specific antigen (Watt et al., 1986) may be used as the receptor for mediated delivery of a nucleic acid in prostate tissue.

In another embodiment of the invention, the expression construct may simply consist of naked recombinant DNA or plasmids. Transfer of the construct may be performed by any of the methods mentioned above which physically or chemically permeabilize the cell membrane. This is applicable particularly for transfer in vitro, however, it may be applied for in vivo use as well. Dubensky et al., (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a CAM also may be transferred in a similar manner in vivo and express CAM.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al, 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

V. Screening Methods Involving Epsin 3

A. Screening for Modulators of Epsin 3

The present invention further comprises methods for identifying modulators of epsin 3 activity. These assays may comprise random screening of large libraries of candidate substances; alternatively, the assays may be used to focus on particular classes of compounds selected with an eye towards structural attributes that are believed to make them more likely to modulate the function of epsin 3.

By function, it is meant that one may assay for a measurable effect on epsin 3 activity. To identify an epsin 3 modulator, one generally will determine the activity or level of inhibition of epsin 3 in the presence and absence of the candidate substance, wherein a modulator is defined as any substance that alters these characteristics. For example, a method generally comprises:

(a) providing a cell expressing a epsin 3 polypeptide;

(b) contacting said cell with a candidate modulator;

(c) measuring epsin 3 expression; and (d) comparing said epsin 3 expression in the presence of said candidate modulator with the expression of epsin 3 in the absence of said candidate modulator;

wherein a difference in the expression of epsin 3 in the presence of said candidate modulator, as compared with the expression of epsin 3 in the absence of said candidate modulator, identifies said candidate modulator as a modulator of epsin 3 expression.

Assays may be conducted in cell free systems, in isolated cells, or in organisms including transgenic animals.

It will, of course, be understood that all the screening methods of the present invention are useful in themselves notwithstanding the fact that effective candidates may not be found. The invention provides methods for screening for such candidates, not solely methods of finding them.

1. Modulators

As used herein the term "candidate substance" refers to any molecule that may potentially inhibit or reduce or enhance or activate epsin 3 activity or expression generally. The candidate substance may be a protein or fragment thereof, a small molecule, or even a nucleic acid molecule. An example of pharmacological compounds will be compounds that are structurally related to epsin 3, or a substrate of epsin 3, such as a nucleic acid molecule. Using lead compounds to help develop improved compounds is know as "rational drug design" and includes not only comparisons with know inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single chain antibodies), each of which would be specific for the target molecule. Such compounds are well known to those of skill in the art. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

An inhibitor or activator/enhancer according to the present invention may be one which exerts its inhibitory or activating effect upstream, downstream or directly on epsin 3. Regardless of the type of inhibitor or activator identified by the present screening methods, the effect of the inhibition or activation by such a compound results in alteration in epsin 3 activity as compared to that observed in the absence of the added candidate substance.

2. In vitro Assays

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. While not directly addressing function, the ability of a modulator to bind to a target molecule in a specific fashion is strong evidence of a related biological effect. For example, binding of a molecule to a target may, in and of itself, be inhibitory, due to steric, allosteric or charge—charge interactions. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

3. In cyto Assays

Primary culture of collagen-activated cells, e.g., keratinocytes, can be utilized for screening of candidate substances.

Cells containing wild-type, natural or mutated epsin 3 may be engineered with indicators that can be used to study various functional attributes of candidate compounds. For example, a normal human epidermal keratinocyte cell line (NHEK) may be engineered to express epsin 3 using GFP expression constructs. In such assays, the compound would be formulated appropriately, given its biochemical nature, and contacted with a target cell expressing epsin 3. Then, various biochemical, molecular or physiological properties may be measured. For example, but not limited to, measuring binding activity, mRNA levels, protein levels, cell migration and endocytosis.

Depending on the assay, culture may be required. As discussed above, the cell may then be examined by virtue of a number of different physiologic assays (cell migration, endocytosis or other assays involved in wound healing and repair). It is also contemplated that effects on expression of other wound-related genes may be measured, for example, EGFR, KGFR. Yet further, it is also within the scope of the present invention to measure the proliferation and differentiation of keratinocytes.

Other cell lines may be used to determine the effectiveness of an epsin 3 inhibitor. For example, cancer cells may be used to determine if an espin 3 inhibitor prevents the invasiveness of cancerous cells. In such assays, the inhibitor would be formulated appropriately, given its biochemical nature, and contacted with a target cancer cells. Then various biochemical, molecular or physiological properties may be measure. For example, but not limited to tumor size or arrest or slowing of tumor progression.

Alternatively, molecular analysis may be performed in which the function of epsin 3 and related pathways may be explored. This involves assays such as those for protein expression, protein function, substrate utilization, mRNA expression (including differential display of whole cell or polyA RNA) and others.

4. In Vivo Assays

The present invention also encompasses the use of various animal models. Specific animal models that are used for wound healing/repair models may be used to determine if overexpression or increased activation of epsin 3 protein enhances or promotes wound healing, e.g., re-epitheliazation. Yet further, it is contemplated that cancer animal models may also be utilized to determine of inhibition of epsin 3 activity prevents the invasiveness of cancerous cells.

Treatment of animals with test compounds will involve the administration of the compound, in an appropriate form, to the animal. Administration will be by any route the could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply and intratumoral injection.

Determining the effectiveness of a compound in vivo may involve a variety of different criteria. Such criteria for epsin 3 ihibitors include, but are not limited to, survival, reduction of tumor burden or mass, arrest or slowing of tumor progression, elimination of tumors, or inhibition or prevention of metastasis. Criteria for epsin 3 activators or enhancers include, but are note limited to, wound healing/repair or re-epithelialization.

VI. Transgenic Animals/Knock-Out/Knock-In Animals

In one embodiment of the invention, transgenic animals are produced which contain a functional transgene encoding a functional epsin 3 polypeptide or variants thereof. Transgenic animals expressing epsin 3 transgenes, recombinant cell lines derived from such animals and transgenic embryos may be useful in methods for screening for and identifying agents that induce or repress function of epsin 3. Transgenic animals of the present invention also can be used as models for studying disease states.

In one embodiment of the invention, a epsin 3 transgene is introduced into a non-human host to produce a transgenic animal expressing a human or murine epsin 3 gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al., 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety). Alternatively, a transgene may also include a tissue-specific promoter to drive the expression of epsin 3 or another gene of interest. The endogenous epsin 3 gene may be replaced by homologous recombination between the transgene and the endogenous epsin 3 resulting in constitutive or enhanced expression of the transgene. This type of transgenic is often referred to as a "knock-in".

It may be desirable to replace the endogenous epsin 3 by homologous recombination between the transgene and the endogenous gene; or the endogenous gene may be eliminated by deletion as in the preparation of "knock-out" animals. Typically, a epsin 3 gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which overexpress epsin 3 or express a mutant form of the polypeptide. Alternatively, the absence of a epsin 3 in "knock-out" mice permits the study of the effects that loss of epsin 3 protein has on a cell in vivo.

As noted above, transgenic animals and cell lines derived from such animals may find use in certain testing experiments. In this regard, transgenic animals and cell lines capable of expressing wild-type or mutant epsin 3 may be exposed to test substances. These test substances can be screened for the ability to enhance wild-type epsin 3 expression and or function or impair the expression or function of mutant epsin 3.

VII. Diagnostic Methods

In some embodiments of the present invention, methods of screening for epsin 3 activity, expression level, and mutation status of the gene or transcript encoding epsin 3 maybe employed as a diagnostic method. Epsin 3 activity may be evaluated using any of the methods and compositions disclosed herein, including assays involving evaluating error rates, fidelity, processivity, and susceptibility to certain compounds that inhibit other polyermases. Any other the compounds or methods described herein may be employed to implement these diagnostic methods.

Assays to evaluate the level of expression of a polypeptide are well known to those of skill in the art. This can be accomplished also by assaying epsin 3 mRNA levels, mRNA stability or turnover, as well as protein expression levels. It is further contemplated that any post-translational processing of epsin 3 may also be evaluated, as well as whether it is being localized or regulated properly. In some cases an antibody that specifically binds epsin 3 may be used.

Furthemore, it is contemplated that the status of the gene may be evaluated directly or indirectly, by evaluating genomic DNA sequence comprising the epsin 3 coding regions and noncoding regions (introns, and upstream and downstream sequences) or mRNA sequence. The invention also includes determining whether any polymorphisms exist in epsin 3 genomic sequences (coding and noncoding). Such assays may involve polynucleotide regions that are identical or complementary to epsin 3 genomic sequences, such as primers and probes described herein.

It is also contemplated that epsin 3 may be a diagnostic marker for pathologies that fail to heal. Such pathologies include, but are not limited to pyogenic granuloma, pyoderma gangrenosum, decubitus ulcers, venous-stasis ulcers, diabetic ulcers, poorly-healing wounds, burns, normal surgical invasions, oral lesions, muscosal lesions, airway/lung lesions, gastric ulcerations, intestinal ulcerations, ulcerative colitis, Chrohn's disease or ophthalmic ulcerations. Yet further, epsin 3 may be a diagnositic for any epithelial cancer that invades through the extracellular matrix, e.g., basal cell carcinoma.

VIII. Therapeutic use of Epsin 3 Modulators

The present invention also contemplates several therapeutic uses for epsin 3 proteins or analogs thereof or epsin 3 modulators. Thus, it is contemplated that epsin 3 or epsin 3 modulators may be administered to an organism in an effective amount to achieve the desired result.

In one embodiment, epsin 3 inhibitors may be administered to an organism. Inhibiting epsin 3 function may prevent the invasiveness of cancerous cells. It is contemplated that the epsin 3 inhibitors may perturb endocytosis and cell migration resulting in the lack of movement of the cancerous cells preventing further invasion into the extracellular matrix.

Another embodiment may comprise increasing the amount of epsin 3 protein or polypeptide. Overexpression of epsin 3 protein may be accomplished using a variety of standard procedures disclosed herein, for example, gene therapy or protein therapy.

Overexpression or increased abundance of epsin 3 protein may enhance the migration of keratinocytes in pathologies that fail to heal. It is contemplated that epsin 3 protein may play a role in any wound or pathology exhibiting altered cell:extracellular matrix interactions. For example, such pathologies include, but are not limited to pyogenic granuloma, pyoderma gangrenosum, decubitus ulcers, venous-stasis ulcers, diabetic ulcers, poorly-healing wounds, burns, normal surgical invasions, oral lesions, muscosal lesions, airway/lung lesions, gastric ulcerations, intestinal ulcerations, ulcerative colitis, Chrohn's disease or opthalmic ulcerations.

A. Genetic Based Therapies

Specifically, the present inventors intend to provide, to a cell, an expression construct capable of providing epsin 3 or a modulator of epsin 3 (an inhibitor or activator/enhancer). The lengthy discussion of expression vectors and the genetic elements employed therein is incorporated into this section by reference. Particularly preferred expression vectors are viral vectors such as adenovirus, adeno-associated virus, herpesvirus, lentivirus, vaccinia virus and retrovirus. Also preferred is liposomally-encapsulated expression vector.

Those of skill in the art are well aware of how to apply gene delivery to in vivo and ex vivo situations. For viral vectors, one generally will prepare a viral vector stock. Depending on the kind of virus and the titer attainable, one will deliver $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$ or $1 \times 10^{12}$ infectious particles to the patient. Similar figures may be extrapolated for liposomal or other non-viral formulations by comparing relative uptake efficiencies. Formulation as a pharmaceutically acceptable composition is discussed below.

B. Protein Therapy

Another therapy approach is the provision, to a subject, of epsin 3, synthetic peptides, mimetics or analogs or epsin 3 modulators thereof. The protein may be produced by recombinant expression means. Formulations would be selected based on the route of administration and purpose including, but not limited to, liposomal formulations and classic pharmaceutical preparations.

C. Combined Therapy

In order to increase the effectiveness of the epsin 3 or epsin 3 modulator, it may be desirable to combine these compositions with an additional agent.

The epsin 3 or epsin 3 modulator may precede, be co-current with and/or follow the other agent(s) by intervals ranging from minutes to weeks. In embodiments where the epsin 3 or epsin 3 modulator, and other agent(s) are applied separately to a cell, tissue or organism, one would generally ensure that a significant period of time did not expire between the time of each delivery, such that the epsin 3 or epsin 3 modulator and agent(s) would still be able to exert an advantageously combined effect on the cell, tissue or organism. For example, in such instances, it is contemplated that one may contact the cell, tissue or organism with two, three, four or more modalities substantially simultaneously (i.e. within less than about a minute) as the epsin 3 or epsin 3 modulator. In other aspects, one or more agents may be administered within of from substantially simultaneously, about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1, about 2, about 3, about 4, about 5, about 6, about 7 or about 8 weeks or more, and any range derivable therein, prior to and/or after administering the epsin 3 or epsin 3 modulator.

Various combination regimens of the epsin 3 or epsin 3 modulator and one or more agents may be employed. Non-limiting examples of such combinations are shown below, wherein a composition epsin 3 or epsin 3 modulator is "A" and an agent is "B":

A/B/A B/A/B B/B/A A/A/B A/B/B B/A/A A/B/B/B

B/A/B/B B/B/B/A B/B/A/B A/A/B/B A/B/A/B A/B/B/A

B/B/A/A B/A/B/A B/A/A/B A/A/A/B B/A/A/A A/B/A/A

A/A/B/A

Administration of the composition epsin 3 or epsin 3 modulator to a cell, tissue or organism may follow general protocols for the administration of chemotherapeutics, taking into account the toxicity, if any. It is expected that the treatment cycles would be repeated as necessary. In particular embodiments, it is contemplated that various additional agents may be applied in any combination with the present invention.

1. Inhibitors and "Anti-Cancer" Agents

An epsin 3 inhibitor may be combined with an agent effective in the treatment of hyperproliferative disease, such as, for example, an anti-cancer agent. An "anti-cancer" agent is capable of negatively affecting cancer in a subject, for example, by killing one or more cancer cells, inducing apoptosis in one or more cancer cells, reducing the growth rate of one or more cancer cells, reducing the incidence or number of metastases, reducing a tumor's size, inhibiting a tumor's growth, reducing the blood supply to a tumor or one or more cancer cells, promoting an immune response against one or more cancer cells or a tumor, preventing or inhibiting the progression of a cancer, or increasing the lifespan of a subject with a cancer. Anti-cancer agents include, for example, chemotherapy agents (chemotherapy), radiotherapy agents (radiotherapy), a surgical procedure (surgery), immune therapy agents (immunotherapy), genetic therapy agents (gene therapy), hormonal therapy, other biological agents (biotherapy) and/or alternative therapies.

More generally, such an agent would be provided in a combined amount with an effective amount of either an epsin 3 inhibitor to inhibit proliferation or invasiveness of a cancer cell. This process may involve contacting the cell(s) with an agent(s) and the epsin 3 inhibitor at the same time or within a period of time wherein separate administration of the epsin 3 inhibitor and an agent to a cell, tissue or organism produces a desired therapeutic benefit. This may be achieved by contacting the cell, tissue or organism with a single composition or pharmacological formulation that includes both a epsin 3 inhibitor and one or more agents, or by contacting the cell with two or more distinct compositions or formulations, wherein one composition includes a epsin 3 inhibitor and the other includes one or more agents.

The terms "contacted" and "exposed," when applied to a cell, tissue or organism, are used herein to describe the process by which a therapeutic construct of epsin 3 inhibitor and/or another agent, such as for example a chemotherapeutic or radiotherapeutic agent, are delivered to a target cell, tissue or organism or are placed in direct juxtaposition with the target cell, tissue or organism. To achieve cell killing or stasis, the epsin 3 inhibitor and/or additional agent(s) are delivered to one or more cells in a combined amount effective to kill the cell(s) or prevent them from migrating or proliferating.

2. Epsin 3 Enhancers and Re-Epithelialization a. Combination with Initiators of Wound Healing Epsin 3 or an enhancer of epsin 3 function may be combined with an agent to enhance wound healing. For example, initiators of wound healing include, but are not limited to keratinocyte growth factor (KGF), platelet derived growth factor (PDGF); basic fibroblast growth factor (bFGF), acidic fibroblast growth factor (aFGF), epidermal growth factor (EGF), transforming growth factor-alpha (TGF-alpha.), transforming growth factor-beta (TGF-beta.), neu differentiation factor (rNDF), insulin-like growth factor I (IGF-1), heparin-binding epidermal growth factor (HB-EGF) and insulin-like growth factor II (IGF-II).

b. Combination with Other Compositions Suitable for Wound Healing

In certain aspects of the present invention, epsin 3 or an enhancer of epsin 3 may be used in combination with any type of wound dressing, for example, but not limited to bandages, gauzes, cotton pads, dressing sheets, artificial skins (i.e., Apligraf®), semipermeable films (i.e., Opsite®, Tegaderm®, Biocclusive®), semiocclusive hydrogels (i.e., Vigilon®, Scherisorb®), and occlusive hydrocolloids (i.e., Duoderm®, Comfeel®, Granuflex®).

It is also contemplated that epsin 3 or an enhancer of epsin 3 may be used in combination with surgical adhesives and tissue sealants which contain plasma proteins that are used for sealing external wounds, such as skin, to reduce blood loss and maintain hemostasis. Such tissue sealants contain blood clotting factors and other blood proteins. FG, also called fibrin sealant, is a gel similar to a natural clot which is prepared from plasma. Typically FG contains a mixture of proteins including traces of albumin, fibronectin and plasminogen. One such example of an FG is Tisseel®.

IX. Formulations and Routes for Administration to Patients

Where clinical applications are contemplated, it will be necessary to prepare pharmaceutical compositions—expression vectors, virus stocks, proteins, antibodies and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The active compounds also may be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient also may be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

X. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Isolation and Culture of Human Keratinocytes

Human keratinocytes were harvested from healthy adult skin from reduction mammoplasties or abdominoplasties as described (Pentland and Needleman, 1986; Sudbeck et al., 1994).

Briefly, the subcutaneous fat and deep dermis were removed, and the remaining tissue was incubated in 0.25% trypsin in PBS at 25° C. After 16 h, the epidermis was separated from the dermis with forceps, and the keratinocytes were scraped into DME. The keratinocyte suspension was added to fresh DME supplemented with 5% fetal calf serum and 0.1% penicillin/streptomycin. Under these culture conditions, keratinocytes proliferate, migrate, differentiate, and cornify similar to cells in vivo (Pentland and Needleman, 1986). A specified amount of keratinocyte suspension was then plated onto tissue culture dishes or coverslips coated with 100 $\mu$g/ml type I collagen, which is necessary for matrix-induced activation. Some cell suspensions were also plated onto dishes coated with 100 $\mu$g/ml gelatin to serve as a negative control as this substrate supports attachment and spreading but does not stimulate activation. Gelatin was prepared by heating native type I collagen for 10 min in an 80° C. water bath (Sudbeck et al., 1997).

Example 2

Identification of Collagen-Regulated Genes in Human Keratinocytes

Primary human keratinocytes were isolated from intact skin and total RNA was harvested immediately following isolation (0 h) or 24 h after plating on type I collagen by phenol-chloroform extraction (Chomczynski and Sacchi, 1987). Any potential contaminating genomic DNA was removed by treating with RQ1 RNase-free DNase (Pilcher et al., 1999). Differential display reverse transcription polymerase chain reaction (ddRT-PCR) was performed on 0 and 24 h RNA samples using the RNAimage® mRNA differential display system (GenHunter Corporation, Nashville, Tenn.) according to the manufacturer's instructions.

Briefly, 0.2 μg DNA-free RNA was used for the reverse transcription reaction with 20 μM dNTPs and 0.2 μM primer H-T$_{11}$G at 65° C. for 5 min, 37° C. for 60 min, 75° C. for 5 min, and 4° C. for 5 min. MMLV reverse transcriptase was added to the reaction mixture after 10 min incubation at 37° C. Amplification of the resultant cDNAs was performed with 1× PCR Buffer, 2.0 μM dNTPs, 0.2 μM arbitrary primer 5'-AAGCTTACGATGC-3' (SEQ ID NO:3), 0.2 μM anchored primer H-T$_{11}$G, 2.0 μl reverse transcription mixture, 0.2 μl $^{35}$S-dATP (2000 Ci/mmol), and 1 unit AmpliTaq polymerase at 94° C. for 30 s, 40° C. for 2 min, and 72° C. for 30 s for 40 cycles. Extension of amplified products was performed at 72° C. for 5 min. 3.5 μl of the amplified samples were resolved on a 6% denaturing polyacrylamide gel. Differentially expressed products were excised from the gel, eluted into ddH$_2$O, and subsequently re-amplified as described above. The amplified cDNAs were then used as probes for Northern hybridization to confirm differential expression. Selection of cDNAs for investigation was limited to genes up- or down-regulated >5-fold in duplicate RNA samples from two individual donors. Confirmed cDNAs were cloned into pGEM®-T easy expression vector and sequenced.

Example 3

Identification and Cloning of Epsin 3

The 143-bp cDNA clone GAP4G1 was sequenced and compared with genes in public databases using BLASTn through the NCBI. One resulting significant match, nucleotides 10237–10379 of Homo sapiens chromosome 17, clone hCIT.22_K_21 (GenBank accession number AC004590), demonstrated 100% sequence identity. To determine if the chromosome 17 genomic clone sequence 5' of the GAP4G1 match coded for a novel gene the internet-based Genscan 1.0 program (http://bioweb.pasteur.fr/seganal/interfaces/genscan.html) was used, which predicts complete gene structures in genomic sequences (Burge and Karlin, 1997). To confirm the predicted gene sequence, the full length cDNA of epsin 3 was amplified by RT-PCR using inter-exonic primers. Alignment of the epsin 3 amino acid sequence with other known epsins was accomplished using the ClustalW program (Thompson et al., 1994) and the dendrogram was generated using results obtained from ClustalW and TreeView software (Page, 1996).

Comparison of the epsin 3 amino acid sequence with human epsins 1 and 2 demonstrated an identical tripartite domain structure common to this protein family. Conserved domains included a COOH-terminal consensus sequence of three NPF repeats that bind Eps15 (Salcini et al., 1997), multiple DPW motifs that bind clathrin AP-2 (Chen et al., 1998; Rosenthal et al., 1999), and a 150 amino acid protein module, the epsin NH$_2$-terminal homology domain (ENTH domain) (Rosenthal et al., 1999). The region of epsin 3 demonstrating the highest sequence identity was the ENTH domain that contained multiple regions of 100% conservation and 80–82% sequence identity with human epsins 1 and 2. Although the DPW and NPF domains of epsin 3 possessed significantly less sequence identity when compared to epsins 1 and 2 (11–28% and 28–34%, respectively), the three NPF motifs were 100% conserved. Furthermore, epsin 3 contained 4 conserved and 5 total DPW motifs, which was consistent with the variability demonstrated among each family member.

Intron/exon junctions of the epsin 3 gene conforming to the GT/AG rule for splice sites (Breathnach and Chambon, 1981) were mapped by comparing cDNA and genomic sequences. Exon-intron boundaries and the sizes of exons and introns are summarized in Table 5. The most notable structural feature of the epsin 3 gene was that exon 1 codes for the 150 amino acid ENTH domain in its entirety. In contrast, the DPW domain encompassed exons 5–7 and the three NPF repeats were found in the distal sequence of exon 8 and throughout exon 9.

TABLE 5

| Exon | Intron-EXON-Intron Junction | Exon Size (bp) | Intron Size (bp) | Genomic DNA Bases* |
|---|---|---|---|---|
| 1 | ATG ACG ACC . . . TCC TAC AAC T gtgagtaag<br>Met Thr Thr . . . Ser Tyr Asn S(er) | 562 | 960 | 3188–3749 |
| 2 | tcattgcag CC TCC TCT TCG . . . GCA GAG AAG gtgaggcca<br>(S)er Ser Ser Ser . . . Ala Glu Lys | 119 | 686 | 4710–4828 |
| 3 | cctccgcag CCT GTC CCC . . . CAC GAG AAG gtagtgggc<br>Pro Val Pro . . . His Glu Lys | 81 | 222 | 5515–5595 |
| 4 | cttctgcag GAG GTG AGG . . . ACC AGC CAG gtagggagt<br>Glu Val Arg . . . Thr Ser Gln | 129 | 931 | 5818–5946 |
| 5 | cctccacag TCC TCC ATC . . . GAC ATC CCA G gtgggcatg<br>Ser Ser Ile . . . Asp Ile Pro G(ly) | 88 | 458 | 6878–6965 |
| 6 | ccatttcag GT TTT AGG CCG . . . GAC ACA CCT G gtaagaaga<br>(G)ly Phe Arg Pro . . . Asp Thr Pro G(ly) | 270 | 166 | 7424–7693 |
| 7 | tcttccgag GT GGT GCC TCG . . . AGC CCT GTG G gtgagcagg<br>(G)ly Gly Ala Ser . . . Ser Pro Val G(lu) | 105 | 130 | 7860–7964 |
| 8 | ctattccag AG CTG GAC CTG . . . TTC CTG ACA G gtaagatat<br>(G)lu Leu Asp Leu . . . Phe Leu Thr G(ly) | 231 | 149 | 8095–8325 |
| 9 | gttctgcag GT CTC AGC GCT . . . CCC TTC CTC tga<br>(G)ly Leu Ser Ala . . . Pro Phe Leu stop | 314 | | 8475–8788 |

In addition to binding Eps15 and AP-2, epsins 1 and 2 exhibited type I cathrin-binding consensus sequences ($^{257}$LMDLADV and $^{283}$LLDLMDAL, respectively) proximal to the DPW domain. An additional motif (LV(D/N)LD) was recently identified within the carboxy-terminal segment of rat epsins 1 and 2 that acts cooperatively with the type I consensus to bind clathrin at an independent site (Drake et al., 2000). Epsin 3 contained a distal $^{506}$LVNDLD low affinity clathrin-binding sequence as well as $^{300}$ILDLADIF proximal to the second DPW repeat, which was reminiscent of a type I consensus as there were two intervening hydrophobic residues between two acidic amino acids.

Comparing human epsin 3 with other known epsins indicated that epsin 3 was most closely related to human and rat epsin 1 (47 and 46%, respectively) and Xenopus Mp90 (44%). In contrast, epsin 3 sequence identity was most divergent from human epsin 2b (39%) and mouse intersectin binding protein 2 (37%), although a significant amount of sequence identity was retained.

Example 4

Northern Analysis and Epsin 3 RT-PCR

Total RNA was harvested from primary keratinocytes, dermal fibroblasts, or umbilical vein endothelial cells as described above and 5 µg/sample was denatured and resolved by electrophoresis through a 1% formaldehyde agarose gel. The RNA was then transferred onto Hybond N+ membrane, cross linked by ultraviolet light, and hybridized with a radiolabeled epsin 3 3' UTR cDNA probe (equivalent to cDNA GAP4G1). To characterize epsin 3 expression in multiple tissues Northern Territory™ Human Normal Tissue Blot II (Invitrogen Corp., Carlsbad, Calif.) and Human RNA Master Blot™ (Clontech Laboratories, Inc., Palo Alto, Calif.) was probed with a radiolabeled epsin 3 cDNA probe according to the manufacturer's instructions. The Northern Territory™ blot contained 20 µg of total RNA per lane and the Human RNA Master Blot™ contained 89–514 ng poly A$^+$ RNA per dot (total amount normalized per blot). RNA from both vendors was pooled from multiple individuals of varying sex and age and confirmed to be free of disease. The cDNA probe was labeled by random priming with [$\alpha$-$^{32}$P] dCTP. Following hybridization, membranes were washed and exposed to x-ray film for an appropriate duration.

Example 5

Epsin 3 RT-PCR

To detect epsin 3 mRNA in various normal, wounded, and pathologic specimens, tissue samples were obtained and immediately immersed in LiN$_2$ to prevent RNAse digestion. Frozen tissues were then homogenized with a polytron in TRIzol reagent (Life Technologies, Rockville, Md.) for RNA isolation. DNase-treated total RNA (1.0 µg) was reverse transcribed with random hexamers using kit reagents and under the manufacturer's recommended conditions (GeneAmp RNA PCR kit, Perkin Elmer Cetus, Norwalk, Conn.). Epsin 3 cDNA was visualized by amplifying a 601 bp fragment corresponding to nucleotides 1–601 of epsin 3. The 3'-antisense primer was complementary to bases 584–601 in exon 2 (5'-GCTCCAGGTCGGAGGTA-3'; SEQ ID NO:4), and the sense primer was defined by bases 1–17 of exon 1 (5'-ATGACGACCTCCGCACT-3'; SEQ ID NO:5) of epsin 3. These primers were to adjacent exons, and thus, the 601 bp DNA produced from epsin 3 mRNA was easily distinguished from products amplified from contaminating DNA or pre-processed mRNA. In addition, the PCR product identity was verified by restriction digestion and sequence analysis. To determine equal loading of RNA an established method to amplify GAPDH by RT-PCR was used (Sudbeck et al., 1997). PCR for epsin 3 was done for 23 cycles and 25 cycles for GAPDH. The resultant products were detected by Southern hybridization using radiolabeled epsin 3 or GAPDH oligonucleotides specific to the amplified cDNA sequence. Hybridization of epsin 3 and GAPDH probes was visualized using a Typhoon 8600 variable mode phosphorimager.

Example 6

Preparation of Antibodies

An 8-chain branching multiple antigenic peptide (MAP) of 20 amino acids, KQNGTKEPDALDLGILGEAL (SEQ ID NO: 6), corresponding to a unique sequence between the DPW and NPF domains of epsin 3 (amino acid residues 464–483 of SEQ ID NO. 2), was used as an antigen.

Rabbits were first immunized with 0.5 mg of the peptide in complete Freund's adjuvant and three booster injections with 0.5 mg of the peptide in incomplete Freund's adjuvant were given 2, 6, and 8 weeks later. Antibodies were collected as whole serum harvested at 10 weeks after primary injection and purified by affinity chromatography with the peptide coupled to NHS Sepharose-4B according to the manufacturer's instructions (Pharmacia).

Example 7

Immunoblotting Assay for Epsin 3

For immunoblotting, primary human keratinocytes were plated onto type I collagen-coated tissue culture dishes and cultured over a time course (0–7 days). Total cell protein was isolated after rinsing cells with 1× phosphate buffered saline (PBS) followed by a 10 min incubation on ice in 200 µl of cell lysis solution (20 mM Tris, 2.0 mM sodium vanadate, 1.0 mM sodium fluoride, 100 mM sodium chloride, 1.0% igepal, 0.5% sodium deoxycholate, 2.0 mM EDTA, 2.0 mM EGTA, and 25 µg each of aprotinin, leupeptin, and pepstatin). Cell lysates were then collected and dounce homogenized 50 times, centrifuged 14,000×G for 10 min, and the supernatant was transferred to new microcentrifuge tubes. 35 µg of total cellular protein was mixed with Laemmli sample buffer containing 10% β-mercaptoethanol and resolved by SDS-PAGE through a 10% gel. Proteins were then electrophoretically transferred to a membrane using a semi-dry transfer apparatus. Membranes were blocked with 5% milk-TBS (20 mM Tris, 150 mM NaCl) for 3 hr and incubated with affinity purified epsin 3 antibodies (1:1000 dil.) in 5% milk-TBS-1% Tween overnight at 4° C. Membranes were washed twice in TBS-Tween and bound antibodies were detected using horseradish peroxidase-linked anti-rabbit secondary antibody (1:2000 dil.). Bound secondary HRP-antibody was detected using LumiGLO® reagent according to the manufacturer's instructions (Cell Signaling Technology, Beverly Mass.).

Example 8

Localization of Epsin 3 in Collagen-Activated Keratinocytes and Cutaneous Wounds by Immunofluorescence Aliquots of keratinocyte cell suspension was plated onto collagen-coated coverslips and cultured for 3 days. For localization in ex vivo cutaneous wounds, punch biopsies of normal human skin (6 mm) were obtained and grown as explant cultures in serum-containing DME for 3 days. Following culture, coverslips were washed twice with PBS, fixed in 4% paraformaldehyde for 1 hr, washed 3× in 0.1 M phosphate buffer, and stored in PBS containing 0.1% sodium azide until staining. Punch biopsy explant cultures were washed 2× in PBS, fixed in 4% paraformaldehyde for 1 hr, washed 3× in 0.1 M phosphate buffer, treated 30 min with 0.05 M Tris, pH 7.4, and immersed in 30% sucrose overnight at 4° C. Explants were embedded in Tissue-Tek® O.C.T. compound (Sikura Finetek, Torrance, Calif.), frozen by $LiN_2$ immersion, and 6 μm-thick sections were cut using a Reichert-Jung cryostat. Tissue sections were then placed onto microscope slides and stored at −20° C.

For immunolocalization of epsin 3, coverslips and explant sections were permeablized by treatment in 80% MeOH for 5 min at 4° C. followed by 100% acetone for 2 min at −20° C., washed 3× for 5 min in PBS, and incubated with 2.5 μg/ml affinity-purified epsin 3 antibodies overnight at 4° C. After 3 washes in PBS, coverslips and slides were incubated with TRITC-conjugated AffiniPure donkey anti-rabbit IgG (Jackson ImmunoResearch Laboratories, Inc., West Grove, Pa.) for 1 hr at room temperature. To visualize epsin 3 and clathrin within the same cells, coverslips were treated with clathrin monoclonal antibody X22 (1:1000 dil.) for 1 hr at room temperature after incubation with anti-epsin 3 antibodies. Clathrin antibody localization was visualized by incubation with Alexa-Fluor™ 488-goat anti-mouse IgG (Molecular Probes, Eugene, Oreg.). Coverslips and slides were then washed 3× in PBS and mounted using Vectashield® mounting medium with DAPI (Vector Laboratories, Inc. Burlingame, Calif.). For negative controls, coverslips and sections were treated with pre-immune serum, secondary IgG alone, or specific/nonspecific peptide-adsorbed epsin 3 antibodies. Digital light photomicrographs were captured with a Polaroid DMC1 camera connected to a Nikon Eclipse E400 microscope. Whole mount immunofluorescence images were captured using a Hammamatsu C4742-9S digital camera connected to a Zeiss Axioplan 2 microscope using OpenLab scientific imaging software (Improvision, Inc., Boston, Mass.). Confocal images were obtained using a Leica TCS SP microscope with Leica TCS NT capturing software.

Example 9

Treatment with Leptomycin B

Keratinocytes were grown on collagen-coated coverslips for three days and subsequently treated with leptomycin B (10 ng/ml; Sigma) or vehicle control for 3.5 hr. After treatment, the cells were fixed and processed for epsin 3 immunofluorescence staining as described herein.

Example 10

Keratinocyte Contact with Collagen Induces Epsin 3 ddRT-PCR was used to compare transcripts expressed in keratinocytes freshly isolated from intact skin or after plating onto fibrillar type I collagen. cDNA clone GAP4G1, an unknown transcript potently induced in keratinocytes following collagen contact, was selected for characterization.

As determined by Northern hybridization, cDNA GAP4G1 hybridized to a single 3.9 kb mRNA species that was induced >20-fold in collagen-activated keratinocytes when compared to cells freshly isolated from unwounded skin. Sequence analysis revealed 100% identity to nucleotides 10237–10379 of human chromosome 17-clone hCIT.22_K_21 (Accession number AC004590). Because this genomic clone had no association with a known gene, the internet-based Genscan 1.0 program was used to determine if the sequence surrounding GAP4G1 contained an open reading frame. A putative gene was identified containing an initiation codon, nine exons, and in frame termination codon that, when translated, coded for a novel 632 amino acid protein with a calculated molecular weight of 68 kDa. To confirm the predicted gene structure, the full length coding sequence was amplified using multiple pairs of gene specific inter-exonic primers. Sequencing of the resultant cDNA demonstrated a 9 exon, 1896 bp open reading frame as predicted. Comparison with known proteins in the public databases using a BLASTp search revealed that the encoded protein had not been previously reported and that it demonstrated remarkable similarity to, but was distinct from, members of the epsin protein family. In addition, a 400 bp fragment unique to exon 7 of epsin 3 was also amplified and used to probe total RNA from freshly isolated and collagen-activated keratinocytes. As before, strong hybridization to a 3.9 kb mRNA was seen only in collagen-activated keratinocytes.

Example 11

Collagen-Mediated Induction of Epsin 3 is Transient and Requires the Native Triple Helical Substrate To determine the molecular mechanisms regulating epsin 3, the expression of this transcript was assessed in keratinocytes at multiple time points following collagen contact. Northern blotting showed that epsin 3 mRNA was absent in keratinocytes freshly isolated from intact skin. Expression was stimulated 12–14 hr after contact with the collagen matrix and became most prominent at 24 hr. This collagen-mediated effect was transient, however, as no epsin 3 mRNA signal was detected at 48 hr, coincident with cells reaching confluence in culture.

The native, triple helical conformation of collagen is requisite for induction of collagenase-1 in keratinocytes as cells plated on gelatin express significantly lower levels of collagenase-1 mRNA and protein, although keratinocyte attachment and spreading is supported by this substrate (Sudbeck et al., 1997). Keratinocytes were plated on fibrillar type I collagen or gelatin to determine if induction of epsin 3 was dependent on the native substrate. As assessed by Northern hybridization, epsin 3 mRNA was reduced by 85% in cells cultured on gelatin when compared to that expressed in cells plated on collagen.

To determine if epsin 3 mRNA was translated, polyclonal antibodies directed against a unique 20 amino acid sequence located between the epsin 3 DPW and NPF domains were generated. Keratinocytes were harvested from normal skin and cultured on collagen over a time course. Total cell proteins were isolated and epsin 3 was visualized by immunoblotting with affinity-purified antibodies. A strongly immunoreactive 68-kDa band was upregulated in keratinocytes 1 day after plating onto collagen and continued to be expressed for the duration of the experiment. In contrast, this protein was absent in cells freshly isolated from intact skin, which was consistent with epsin 3 mRNA induction in activated keratinocytes following collagen contact.

A second, smaller unknown immunoreactive band of approximately 50-kDa was visualized in keratinocyte cell lysates, but its expression was not affected by contact with collagen, suggesting that the antibody bound a nonspecific protein or a currently uncharacterized species. Specificity of the affinity purified antibody was verified by pre-adsorption with the antigenic peptide or a peptide made from another unique epsin 3 sequence prior to Western immunoblotting. As predicted, no bands were seen in immunoblots probed with the antigenic peptide adsorbed antibody, whereas the nonspecific peptide had no effect.

Example 12

Collagen-Activated Epsin 3 Partially Co-Localizes with Clathrin and Shuttles to the Nucleus To assess the subcellular distribution of epsin 3, keratinocytes were plated onto collagen-coated coverslips and processed for immunofluorescence staining using affinity purified epsin 3 antibodies.

Following three days on collagen, keratinocytes exhibited prominent immunoreactivity for epsin 3 that localized to intracellular vesicles throughout the cytoplasm and concentrated in the perinuclear region. These findings are consistent with previous reports documenting the localization of epsins 1 and 2 in other cell types (Chen et al., 1998; Drake et al., 2000). Processing cells with pre-immune serum resulted in non-specific staining as only the outlines of suprabasal cells were highlighted.

Epsin 1 binds to clathrin directly and intracellular distribution studies have shown that a portion of the total epsin pool associates with clathrin coated structures (Chen et al., 1998; Drake et al., 2000). To determine if epsin 3 demonstrated a similar pattern of localization, cells were double labeled with affinity purified epsin 3 antibodies and monoclonal antibody X22 directed against the clathrin heavy chain. Consistent with the behavior of epsins 1 and 2, a subpopulation of epsin 3 co-localized to clathrin-coated structures. Vesicles that exhibited double labeling were predominantly located at the cell periphery where clathrin coated pits would be assembling, whereas epsin 3 immunoreactivity was absent from a pool of clathrin located near the nucleus, presumably at the trans-Golgi network (Drake et al., 2000). This data demonstrates that the epsin 3 protein functions similarly to other epsins.

Resolution of the epsin 1 ENTH domain crystal structure has revealed remarkable structural similarity to β-catenin armadillo repeats (Hyman et al., 2000). In addition to its involvement in endocytosis, epsin 1 is capable of interacting with the transcription factor promyelocytic leukemia $Zn^{2+}$ finger protein and translocating to the nucleus where it may regulate transcription (Hyman et al., 2000). Because the epsin 3 ENTH domain is highly conserved, epsin 3 may exhibit similar behavior.

To determine the ability of epsin 3 to shuttle between the nucleus and cytoplasm, collagen-activated keratinocytes were treated with leptomycin B, an antifungal antibiotic that blocks the Crm1-dependent nuclear export pathway and induces the nuclear accumulation of proteins that have shuttling activity (Nishi et al., 1994; Kudo et al., 1999; van Hengel et al., 1999). Epsin 3 in keratinocytes treated transiently with leptomycin B accumulated in the nucleus (arrowheads), whereas control cells treated with vehicle alone exhibited prominent cytoplasmic localization.

These data suggest that epsin 3 may play a dual role in regulating keratinocyte behavior during migration as well as transcription of genes, thereby establishing a novel signaling mechanism connecting the endocytic machinery with the nucleus. Potential functions of nuclear epsin 3 in keratinocytes may be prolongation of the wound healing response by stimulating activation specific genes or induction of basement membrane and cellular proteins required for differentiation as re-epithelialization is completed.

Example 13

Epsin 3 is Expressed by Migrating Keratinocytes

Keratinocytes grown on collagen under high calcium (1.8 mM) conditions recapitulate the epidermal wound healing response by forming subpopulations of migrating, proliferating, and differentiating cells (Pentland and Needleman, 1986). When viewed from above, differentiating keratinocytes are seen as islands of confluent cells surrounded by hyperproliferative cells. Bordering the hyperproliferative cells, and often detached from them, are migrating keratinocytes.

To determine if the expression of epsin 3 protein was spatially restricted, keratinocytes were isolated from intact skin and suspensions of low or high cell density were plated onto collagen-coated coverslips. The low-density cell suspension prolonged individual migrating keratinocytes for the duration of the experiment, whereas the larger cell density suspension promoted cell:cell contact that resulted in the formation of differentiating islands. In cultures predominantly made up of individual, migrating keratinocytes, epsin 3 was prominently expressed in all cells examined. In differentiation promoting cultures, however, epsin 3 was spatially confined to keratinocytes migrating away from and bordering islands of differentiating cells. Clathrin expression was not restricted to a particular cell population as positive staining was noted in both migrating and differentiating keratinocytes. Co-localization of epsin 3 with clathrin was evident in the migrating cells as seen previously.

Example 14

Epsin 3 is Expressed by Migrating Keratinocytes in Cutaneous Wounds

Briefly, punch biopsies of normal human skin were cultured ex vivo over a time course and processed for immunofluorescence staining using affinity purified epsin 3 antibodies. During the culture period, keratinocytes at the cut edge of the biopsy undergo a wound healing response and are activated to migrate off of the basement membrane and onto the denuded dermis. It has been previously demonstrated in previous studies that expression of collagenase-1 in this model mirrors that seen in vivo (Pilcher et al., 1999).

Following three days, epsin 3 immunoreactivity was predominantly localized to basal keratinocytes within the migrating epithelial tongue. Higher magnification of epsin 3 expressing keratinocytes demonstrated a vesicular staining pattern consistent with that observed in collagen-activated keratinocytes. Paralleling the in vitro data, epsin 3 was specifically localized to basal keratinocytes at the cell:extracellular matrix interface, whereas suprabasal differentiating cells in the migrating tongue exhibited only background staining. Epsin 3 signal progressively diminished away from the wound edge and was detectable at low levels in only a few basal cells of intact epidermis. Immunoreactivity was also noted in a subpopulation of cells scattered throughout the dermis, most of which had a fibroblast-like appearance. No specific staining was detected in samples processed with pre-immune serum or epsin 3 antibodies pre-adsorbed with antigenic peptide.

Thus, these findings demonstrated that epsin 3 was expressed in a restricted manner unlike the previously described members of this protein family. More specifically, this data underscores the profound influence that collagen contact has on keratinocyte behavior during wound healing and supports the suggestion that in addition to soluble factors, contact with dermal extracellular matrix induce keratinocyte activation by stimulating the expression of transcripts required for repair.

Example 15

Epsin 3 Expression is Restricted to Epithelial Wounds and Pathologies with Altered Cell:Extracellular Matrix Interactions The expression of epsin 3 was analyzed in various tissues. Briefly, total RNA from multiple tissues was isolated, probed with an epsin 3 cDNA probe and hybridized. Epsin 3 was not expressed in multiple fetal or most adult tissues examined (summarized in Table 6). A low level of epsin 3 mRNA (0.3-fold over background) was detected in adult stomach, but only after extended exposure of the x-ray film. This finding was variable, however, as hybridization was not found in stomach total RNA obtained from a separate pool of RNA donors. In addition, dermal fibroblasts and endothelial cells, two additional cell types activated during wound repair were also screened. Epsin 3 was not detected in total RNA harvested from resting or activated cells.

TABLE 7

Expression of Epsin 3 mRNA in Cultured Human Cells and Tissues

| Cell/Tissue Examined | Level of Expression |
| --- | --- |
| Collagen-Activated Keratinocytes | +++++ |
| Chronic Wound | +++ |
| Basal Cell Carcinoma | +++ |
| Ulcerative Colitis | +++ |
| Unwounded Skin | Neg. |
| Stomach | +/− |
| Dermal Fibroblasts (±PMA, IL-1β) | Neg. |
| Endothelial Cells (±PMA, IL-1β, TNF-α) | Neg. |
| Brain and Spinal Cord (Fetal and Adult) | Neg. |
| Heart and Aorta (Fetal and Adult) | Neg. |
| Skeletal Muscle and Adipose | Neg. |
| Esophagus, Duodenum, Appendix, Colon | Neg. |
| Liver, Pancreas, Spleen, Thymus | Neg. |
| Lung and Trachea | Neg. |
| Kidney, Prostate, Bladder | Neg. |
| Uterus, Placenta, Ovary, Testis | Neg. |
| Pituitary, Thyroid, Adrenal, Salivary, and Mammary Gland | Neg. |
| Peripheral Leukocyte, Lymph Node, Bone Marrow | Neg. |

Because epsin 3 was not expressed in any resting tissues or cultured cells examined (with the exception of collagen-activated keratinocytes), the data suggest that expression is specific to wounded or pathologic tissues in which epithelial cells undergo altered cell:extracellular matrix interactions. This may explain the results demonstrating variable and low levels of epsin 3 mRNA in stomach, as the pooled samples may have been contaminated with wounded tissue (i.e. gastric ulceration). Expression of epsin 3 in wounded or pathologic tissues was determined by amplifying a 601 bp fragment of epsin 3 by RT-PCR. Epsin 3 mRNA was expressed in total RNA isolated from chronic cutaneous wound, basal cell carcinoma and ulcerative colitis, all wounds or pathologies that undergo altered cell:extracellular matrix interactions. In contrast, expression was not found in normal, unwounded skin.

This data demonstrates that epsin 3 was not expressed in resting, homeostatic tissues, but rather in epithelial wounds or pathologies that typically exhibit a disrupted basement membrane (i.e., cutaneous wound, basal cell carcinoma, and ulcerative colitis). This is in marked contrast to other epsins, which are widely distributed in resting tissues, and suggests that epsin 3 may play a significant role in regulating cellular function of epithelial cells during events that require cell migration.

Example 16

Molecular Mechanisms of Collagen-Induced Epsin 3 Expression in Keratinocytes

In contrast to collagen-mediated induction of MMP-1, which occurs within 2 hr of matrix contact (Mansbridge and Knapp, 1987), epsin 3 mRNA was not apparent until after 24 hr. However, like MMP-1, expression of epsin 3 was induced markedly, becoming most prominent at 24 hr followed by a decrease at 48 hr. Although the timecourse of MMP-1 and epsin 3 induction differed by 8 hours, it appears that similar intracellular signaling pathways were required to induce each gene.

It is known that collagen-mediated induction of keratinocyte MMP-1 requires, at least in part, ERK 1/2 MAP kinase activity. Thus, kertinocytes were assayed to determine if epsin 3 requires ERK 1/2 MAP. Briefly, keratinocytes were pretreated with various signaling inhibitors prior to plating on collagen-coated dishes. MMP-1 and epsin 3 mRNAs were both inhibited when co-cultured in the presence of ERK 1/2 inhibitor PD98059 (45 and 70%, respectively), suggesting that common signaling pathways mediate collagen induction of each transcript.

Example 17

In vivo Expression Pattern of Epsin 3 in Normal, Wounded, and Diseased Tissues

In situ hybridization (ISH) and immunohistochemistry (IHC) techniques allow for the localization of epsin 3 in a variety of wound scenarios. For example, but not limited to ISH and IHC allow for an assessment of expression in tissue sections from a panel of epidermal wounds that exhibit a disrupted basement membrane, including full-thickness acute wounds and chronic wounds such as pyogenic granuloma, pyoderma gangrenosum, decubitis ulcers, and non-specific ulcers.

ISH may use an $^{35}$S-labeled antisense epsin 3 cDNA probe (Mansbridge and Knapp, 1987). Briefly, sections from both healthy individuals and uninvolved areas of diseased skin are probed to confirm that epsin 3 expression is confined to the wounded tissue. Sections from bullous pemphigoid, a blistering disease where lesions form above the BM, provides further insight into the determination if epsin 3 expression is specific to wounds where the BM is disrupted. To determine antisense probe specificity, sections of epsin 3-positive tissue are hybridized with a sense-strand probe.

Epsin 3 protein is further assessed in acute and chronic wounds by IHC. Synthetic peptide-based polyclonal antibodies directed against epsin 3 were generated or may be obtained commercially through Research Genetics, Inc. (Huntsville, Ala.). Briefly, three purified synthetic peptides (each 21 amino acids) from regions unique to human epsin 3 are injected into two New Zealand white female rabbits. Two booster injections are performed at regular intervals and serum samples collected on days 28, 56, and 70 to determine antibody titer. Each antibody is purified using synthetic peptide-conjugated affinity columns and subsequently used to localize epsin 3 protein in epidermal wound samples as described above. Samples are incubated with non-immune IgG to confirm antibody specificity. It is further envisioned that expression is assessed by screening for RNA message by Northern blotting, quantitative PCR or other mechanism well known to one of skill.

Example 18

Additional Molecular Mechanism(s) Regulating Induction of Keratinocyte Epsin 3

Data suggest that keratinocyte contact with collagen induces a number of transcripts involved in, and potentially required for, the wound healing response. Indeed, MMP-1 expression is required for keratinocyte migration and contact with collagen is the critical determinant mediating this response (Mansbridge and Knapp, 1987; Paladini et al., 1996). However, despite the abundance of type I collagen, the wound environment is complex and contains numerous extracellular matrix components and growth factors. Wound edge keratinocytes are therefore required to process multiple extracellular signals prior to activation of the migratory phenotype.

Dermal and provisional extracellular matrix substrates that are likely to contact wound edge keratinocytes (type III collagen, elastin, tenascin, laminin-5, fibronectin, and vitronectin) are tested for their ability to induce expression of epsin 3 independently of collagen. Briefly, keratinocytes are cultured on physiologically relevant concentrations of each extracellular matrix protein and epsin 3 expression determined by Northern hybridization and Western immunoblotting. Keratinocyte RNA or protein isolated from intact skin serve as negative controls.

Because ERK 1/2 activity is required for both MMP-1 and epsin 3 expression in keratinocytes, it appears that common signaling pathways from the cell surface to the nucleus are necessary for collagen-mediated induction of both genes. Previous studies have shown that induction of MMP-1 requires native type I collagen (Mansbridge and Knapp, 1987), α2 integrin signaling (Paladini et al, 1996), ERK 1/2 activity, and an intermediate EGFR autocrine loop (Sudbeck et al., 1994). In order to determine whether a specific receptor is required for epsin 3 induction, keratinocytes isolated from intact skin are pre-incubated with control media or medium containing blocking antibodies directed against integrin subunits α 3, α 2, or β 1. Keratinocytes are then plated onto collagen and epsin 3 induction assessed as described. Parallel experiments are run to determine if multiple post-integrin signaling pathways are required for induction of epsin 3. Partial inhibition of epsin 3 following treatment with ERK 1/2 inhibitor PD98059 suggests that multiple signaling pathways may be required following integrin activation. In order to make this determination, primary keratinocytes are pre-incubated with combinations of specific intracellular signaling pathway inhibitors (e.g., jun kinase, p38 kinase, MAPK, PLC) potentially involved in collagen-mediated induction of epsin 3. Cells are then plated onto collagen and epsin 3 expression determined as described above.

Example 19

Physiologic Shuttling of Epsin 3 to the Nucleus of Differentiating Keratinocytes Briefly, primary human keratinocytes were isolated and cultured on type I collagen (100 μg/ml) over a time course (0–5 days).

Initially, epsin 3 expression was induced following collagen contact and was evident in cells (Day 3) as punctate vesicles throughout the cytoplasm co-localized partially with clathrin. As the keratinocytes proliferated, cell—cell contacts were established and the cells reverted from a migratory phenotype and began to differentiate (Day 5). When localization was evaluated in these cultures, epsin 3 was evident only in the nucleus, whereas the few remaining migrating keratinocytes retained the punctate cytoplasmic localization.

Thus, these results suggest that epsin 3 may have a dual function: 1) enhancing endocytosis in migrating keratinocytes and 2) stimulating the expression of differentiation-specific genes when it translocates to the nucleus as migration ceases.

Example 20

Functional Studies for Epsin 3 Expression in Collagen-Activated Keratinocytes

The functional significance of both cytoplasmic (endocytosis) and nuclear (differentiation) localization of epsin 3 in collagen-activated keratinocytes was studied.

Briefly, two expression constructs containing a full-length epsin 3 tagged with a FLAG and GFP epitopes were made. Next, normal human epidermal keratinocytes (NHEK) were transfected with the Ep3-GFP construct. After transfection, cytoplasmic vesicles in the expressing cells were visualized. These results are consistent with epsin 3 function in endocytosis.

To further characterize epsin 3 function, additional construcst are made such as multiple deletion constructs, point mutant constructs, etc. These constructs are used to express mutant forms of the epsin 3 protein in an attempt to determine if function is required for migration and differentiation.

Because epsin 3 does not possess a nuclear localization sequence, it is necessary to identify the transcription factor-binding domain. To identify the transcription factor-binding domain, the binding domain is mutated to block epsin 3 accumulation within the nucleus and determine if keratinocyte differentiation is altered.

To further characterize the function of epsin 3, an expression construct is made to induce nuclear accumulation of epsin 3. The construct is made by adding a nuclear localization sequence to the sequence encoding epsin 3. After transfection of the construct, keratinocyte behavior is monitored to determine the effects of increased nuclear accumulation of epsin 3 on keratinocyte behavior.

Example 21

Therapeutic Uses of Epsin 3

The ability of keratinocytes to respond to injury requires the processing of multiple extracellular signals, including soluble ligands binding to cognate receptors and exposure to new extracellular matrix. Signaling through receptor tyrosine kinases by growth factors such as EGF, keratinocyte growth factor (KGF), and TGF-α elicits a number of transient cell responses including enhanced cell proliferation and migration (Clark, 1996). As healing progresses, however, epidermal cells lose their responsiveness to these signals and revert to a gene expression program that promotes differentiation. Activated growth factor receptors, such as the EGFR (Sorkin and Waters, 1993) and KGFR (Marchese et al., 1998), are rapidly internalized via endocytosis as cell migration ceases and this pathway serves as an important regulatory mechanism to control cell surface receptor expression and downstream signaling events. A mechanism by which activated receptors are internalized via epsin 3-enhanced endocytosis would have profound effects on the ability of keratinocytes to respond to extracellular stimuli and mediate the wound healing response.

Overexpression or increased abundance of epsin 3 protein may enhance or promote wound repair. Standard gene therapy or protein therapy is used to increase the amount of epsin 3 protein in wounded tissue. Epsin 3 protein is delivered directly or in-directly to the wounded tissue using standard pharmaceutical delivery techniques well known to those of skill in the art. Yet further, epsin 3 is used in combination with well-known therapies to enhance wound repair. For example, epsin 3 and EGF are given in amounts that efficiently enhance wound repair.

Expression of espin 3 may also be used as a therapeutic for such skin disorderes as psoriasis, where epsin 3 is not expressed and keratinocytes are hyperproliferative. It is envisioned that inducing expression and targeting nuclear accumulation of epsin 3 in psoriatic keratinocytes would lead to induction of differentiation and inhibition of the hyperproliferative state. Yet further, any pathology or wound exhibiting altered cell:extracellular matrix interactions may be a potential candidate for epsin 3 gene therapy as described above.

Example 22

Therapeutic Uses of Epsin 3 Inhibitor

An epsin 3 inhibitor may block or perturb the function of epsin 3 in endocytosis and cell migration, thus preventing the invasiveness of cancerous cells.

An epsin 3 inhibitor is given in a pharmaceutically acceptable amount to a patient suffering from an invasive epithelial type cancer, e.g., basal cell carcinoma. The inhibitor is given in amounts determined effective by one of skill in the art. Yet further, an epsin 3 inhibitor is used in combination with other standard anti-cancer agents.

Example 23

Epsin 3 as a Diagnostic Marker

The strict regulation of epsin 3 expression may serve as a marker for tissues undergoing wound healing or repair or for malignancy.

Samples are isolated from tissues suspected of wound healing or malignancy. Epsin 3 is measured by a variety of standard techniques that have been described herein. Such techniques include, but are not limited to Northern hybridization, Western hybridization or RT-PCR.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Australian Patent 75097/87
European Application No. 320 308
European Application No. 329 822
GB Application No. 2 202 328
PCT Application No. PCT/US87/00880
PCT Application No. PCT/US89/01025
PCT Application WO 88/10315
PCT Application WO 89/06700
U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,554,101
U.S. Pat. No. 4,683,195
U.S. Pat. No. 4,683,202
U.S. Pat. No. 4,800,159
U.S. Pat. No. 4,879,236
U.S. Pat. No. 4,883,750
U.S. Pat. No. 5,354,855
U.S. Pat. No. 5,693,762
U.S. Pat. No. 5,843,650
U.S. Pat. No. 5,843,663
U.S. Pat. No. 5,846,709
U.S. Pat. No. 5,846,783
U.S. Pat. No. 5,849,481
U.S. Pat. No. 5,849,486
U.S. Pat. No. 5,849,497
U.S. Pat. No. 5,849,546
U.S. Pat. No. 5,849,547
U.S. Pat. No. 5,851,772
U.S. Pat. No. 5,858,652
U.S. Pat. No. 5,861,155
U.S. Pat. No. 5,866,366
U.S. Pat. No. 5,871,986
U.S. Pat. No. 5,882,864
U.S. Pat. No. 5,900,481
U.S. Pat. No. 5,912,148
U.S. Pat. No. 5,916,776
U.S. Pat. No. 5,916,779
U.S. Pat. No. 5,919,626
U.S. Pat. No. 5,922,574
U.S. Pat. No. 5,925,565
U.S. Pat. No. 5,928,905
U.S. Pat. No. 5,928,906
U.S. Pat. No. 5,932,451
U.S. Pat. No. 5,935,819
U.S. Pat. No. 5,935,825
U.S. Pat. No. 5,939,291
U.S. Pat. No. 5,942,391
U.S. Pat. No. 6,020,192
U.S. Pat. No. 6,054,297
U.S. Pat. No. 4,427,650
U.S. Pat. No. 4,427,651
U.S. Pat. No. 4,627,879

U.S. Pat. No. 4,928,603
U.S. Pat. No. 4,714,457
U.S. Pat. No. 5,030,215
U.S. Pat. No. 4,932,942
Abbondanzo et al., *Am. J. Clin. Pathol.,* 93(5):698–702, 1990.
Allred, et al., *Arch Surg.,* 125(1):107–113, 1990.
Almendro et al., *J. Immunol.,* 157(12):5411–5421, 1996.
Ausubel, et al., In: *Molecular Biology. Current Protocols,* Greene and Wiley, Harvard Medical School, 1996.
Baichwal and Sugden, In: *Gene transfer,* Kucherlapati (ed.), NY Plenum Press, 117–148, 1986.
Bellus, *J. Macromol. Sci. Pure Appl. Chem.,* A31(1):1355–1376, 1994.
Berzal-Herranz et al., *Genes and Devel.,* 6:129–134, 1992.
Breathnach and Chambon, *Annu Rev Biochem* 50, 349–83, 1981.
Brown et al., *Breast Cancer Res. Treat.,* 16:192, 1990.
Burge et al., *J Mol Biol* 268(1), 78–94, 1997.
Byrne et al., *Br. J. Surg.* 78:841–843, 1991.
Capaldi et al., *Biochem. Biophys. Res. Comm.,* 76:425–433, 1977.
Carbonelli et al., *FEMS Microbiol Lett.* 177(1):75–82, 1999.
Cech et al., *Cell,* 27:487–496, 1981.
Chandler et al., *Proc Natl Acad Sci USA,* 94(8):3596–3601, 1997.
Chen et al., *Nature* 394(6695), 793–7, 1998
Chomczynski and Sacchi *Anal Biochem* 162(1), 156–9, 1987.
Chowrira et al *J Biol Chem.,* 268:19458–19462, 1993.
Clark et al *J. Invest. Dermatol.,* 79:264–269, 1982.
Clark, *The molecular and cellular biology of wound repair.,* 2nd Ed. (Clark, Ed.), Plenum Press, New York, 1996.
Cocea, *Biotechniques,* 23:814–816, 1997.
Coulombe, *Biochem. Biophys. Res. Commun.,* 236(2):231–238, 1997.
Coupar et al., *Gene,* 68:1–10, 1988.
De Jager R. et al., *Semin Nucl Med* 23(2):165–179, 1993.
Doolittle and Ben-Zeev, *Methods Mol Biol.,* 109:215–237, 1999.
Drake et al., *J Biol Chem* 275(9), 6479–6489, 2000.
Forster and Symons, *Cell,* 49:211–220, 1987.
Friedmann, *Science,* 244:1275–1281, 1989.
Gerlach et al., *Nature,* 328:802–805, 1987.
Gibble et al., *Transfusion* 30:741–747, 1990.
Grinnell, *J. Trauma* 30:S 144–S149, 1990.
Gulbis and Galand, *Hum Pathol* 24(12):1271–1285, 1993.
Guo et al., *J. Biol. Chem.* 272(1), 24–27, 1997.
Harlow and Lane, In: *Antibodies: A laboratory Manual,* Cold Spring Harbor Laboratories, Cold Spring Harbor, N.Y., 1988.
Haseloff and Gerlach, *Nature,* 334:585–591, 1988.
Hedelin et al., *Eur. Surg. Res.* 15:31, 1983.
Hermonat and Muzyczka, *Proc Nat'l. Acad. Sci. USA,* 81:6466–6470, 1984.
Hertle et al., *Development* 112, 193–206, 1991.
Horwich et al. *J. Virol.,* 64:642–650, 1990.
Hyman et al., *J Cell Biol* 149(3), 537–46, 2000.
Innis et al., *Proc Natl Acad Sci USA.* 85(24):9436–9440, 1988.
Inoue et al., *J. Invest. Dermatol.* 104, 479–483, 1995.
Inouye et al., *Nucl. Acids Res.,* 13:3101–3109, 1985.
Johnson et al., In: *Biotechnology And Pharmacy,* Pezzuto et al., eds., Chapman and Hall, New York, 1993.
Joyce, *Nature,* 338:217–244, 1989.
Juhasz et al., *Am. J. Pathol.* 143, 1458–1469, 1993.
Kim and Cech, *Proc. Natl. Acad. Sci. USA,* 84:8788–8792, 1987.
Kraus et al., *FEBS Lett.,* 428(3):165–170, 1998.
Kudo et al., *Proc Natl Acad Sci USA* 96(16), 9112–7, 1999.
Kwoh et al., *Proc Natl Acad Sci USA.* 86(4):1173–1177, 1989.
Kyte and Doolittle *J. Mol. Biol.,* 157(1):105–132, 1982.
Lareyre et al., *J Biol Chem.,* 274(12):8282–8290, 1999.
Le Varlet et al., *J Dermatol Sci* 2(4), 287–99, 1991.
Lee et al., *J Auton Nerv Syst.* 74(2–3):86–90, 1997.
Lerner et al., *J. Surg. Res.* 48:165–181, 1990.
Levenson et al., *Human Gene Therapy,* 9:1233–1236, 1998.
Lieber and Strauss, *Mol. Cell. Biol.,* 15: 540–551, 1995.
Macejak and Sarnow, *Nature,* 353:90–94, 1991.
Mansbridge and Knapp, *J. Invest. Dermatol.* 89(3):253–263, 1987.
Marchese et al., *J Cell Sci* 111 (Pt 23), 3517–27, 1998.
McPherson et al., *Biochem Biophys Res Commun* 244(3), 701–5, 1998.
Michel and Westhof, *J. Mol. Biol.,* 216:585–610, 1990.
Nakamura et al., In: *Enzyme Immunoassays: Heterogeneous and Homogeneous Systems, Chapter 27,* 1987.
Nicolas and Rubinstein, In: *Vectors: A survey of molecular cloning vectors and their uses,* Rodriguez and Denhardt (eds.), Stoneham: Butterworth, pp. 494–513, 1988.
Nishi et al., *J Biol Chem* 269(9), 6320–4, 1994.
Nomoto et al., *Gene,* 236(2):259–271, 1999.
Page, *Comp. App. in the Biosci.* 12, 357–358, 1996.
Paladini et al., *J. Cell Biol.,* 132(3):381–397, 1996.
Palukaitis et al., *Virology,* 99:145–151, 1979.
Pelletier and Sonenberg, *Nature,* 334:320–325, 1988.
Pentland and Needleman *Clin. Invest.* 77, 246–251, 1986.
Perriman et al., *Gene,* 113:157–163, 1992.
Pilcher et al., *Arch Dermatol Res* 290 Suppl, S37–46, 1998.
Pilcher et al., *J Biol Chem* 274(15), 10372–81, 1999.
Pilcher et al., *J Cell Biol* 137(6), 1445–57, 1997.
Prody et al., *Science,* 231:1577–1580, 1986.
Reinhold-Hurek and Shub *Nature,* 357:173–176, 1992.
Ridgeway, In: *Vectors: A survey of molecular cloning vectors and their uses.* Rodriguez and Denhardt, eds. Stoneham: Butterworth, pp. 467–492, 1988.
Rosenthal et al., *J Biol Chem* 274(48), 33959–65, 1999.
Saarialho-Kere et al., *J. Clin. Invest.* 90, 1952–1957, 1992.
Saarialho-Kere et al., *J. Clin. Invest.* 92, 2858–2866, (1993).
Salcini et al., *Genes Dev* 11(17), 2239–49, 1997.
Sambrook et al., *Molecular Cloning: A Laboratory Manual,* 2nd Ed., Cold Spring Harbor Press, Cold Spring Harbor, N.Y., 1989.
Sarver et al., *Science,* 247:1222–1225, 1990.
Scanlon et al., *Proc Natl Acad Sci USA,* 88:10591–10595, 1991.
Sioud et al., *J Mol. Biol.,* 223:831–835, 1992.
Sorkin and Waters *Bioessays* 15(6), 375–82, 1993.
Sudbeck et al., *J Biol Chem* 272(35), 22103–10, 1997.
Sudbeck et al., *J. Biol. Chem.* 269, 30022–30029, 1994.
Symington et al., *J. Cell Biol.* 120, 523–535, 1993.
Symons, *Annu. Rev. Biochem.,* 61:641–671, 1992.
Temin, In: *Gene Transfer,* Kucherlapati (ed.), New York: Plenum Press, pp. 149–188, 1986.
Thompson et al., *Nucleic Acids Res* 22(22), 4673–80, 1994.
Thompson et al., *Nature Genet.,* 9:444–450, 1995.
Tsumaki et al., *J Biol Chem.* 273(36):22861–22864, 1998.
van Hengel et al., *Proc Natl Acad Sci USA* 96(14), 7980–5, 1999.
Wada et al., *Nucleic Acids Res.* 18:2367–2411, 1990.
Walker et al., *Nucleic Acids Res.* 20(7):1691–1696, 1992.
Wang et al., *J. Biol Chem* 270(17), 10079–83, 1995.
Woodley et al., *J. Invest. Dermatol.* 4, 418–423, 1986.
Wu et al., *Biochem Biophys Res Commun.* 233(1):221–226, 1997.
Yamada et al., In: *The Molecular and Cellular Biology of Wound Repair,* second edition (Clark, R. A. F., ed), pp. 311–338, Plenum Press, New York, 1996.
Yuan and Altman, *Science,* 263:1269–1273, 1994.
Yuan et al., *Proc. Natl. Acad. Sci. USA,* 89:8006–8010, 1992.
Zhao-Emonet et al., *Gene Ther.* 6(9):1638–1642, 1999.

What is claimed is:

1. An isolated and purified polynucleotide comprising a nucleic acid sequence encoding polypeptide of SEQ ID NO:2.

2. The polynucleotide of claim 1, comprising the nucleic acid sequence set forth in SEQ ID NO:1.

3. An expression vector comprising a promoter operably linked to a nucleic acid sequence that encodes SEQ ID NO:2.

4. The expression vector of claim 3, wherein the expression vector is a viral vector.

5. The expression vector of claim 3, wherein the nucleic acid sequence comprises the nucleic acid sequence of SEQ ID NO:1.

6. The expression vector of claim 3, wherein the expression vector is a nonviral vector.

7. The expression vector of claim 6, wherein the vector is comprised in a liposome.

8. A vector comprising the polynucleotide of claim 1.

9. A vector comprising the polynucleotide of claim 2.

* * * * *

UNITED STATES PATENT AND TRADEMARK OFFICE
CERTIFICATE OF CORRECTION

PATENT NO.     : 6,720,180 B2
DATED          : April 13, 2004
INVENTOR(S)    : Brian K. Pilcher It is certified that error appears in the above-identified patent and that said Letters Patent is hereby corrected as shown below:

Column 81,
Line 30, after "encoding", insert -- the -- therefor.

Signed and Sealed this

Sixteenth Day of November, 2004

JON W. DUDAS
*Director of the United States Patent and Trademark Office*